US012007396B2

(12) United States Patent
Chen et al.

(10) Patent No.: US 12,007,396 B2
(45) Date of Patent: Jun. 11, 2024

(54) METHODS FOR CHARACTERIZING LOW-ABUNDANCE HOST CELL PROTEINS

(71) Applicant: Regeneron Pharmaceuticals, Inc., Tarrytown, NY (US)

(72) Inventors: I-Hsuan Chen, Redwood City, CA (US); Hui Xiao, Ridgewood, NJ (US); Ning Li, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 335 days.

(21) Appl. No.: 17/217,518

(22) Filed: Mar. 30, 2021

(65) Prior Publication Data
US 2021/0302433 A1    Sep. 30, 2021

Related U.S. Application Data

(60) Provisional application No. 63/001,690, filed on Mar. 30, 2020, provisional application No. 63/031,336, filed on May 28, 2020.

(51) Int. Cl.
*G01N 33/68*     (2006.01)

(52) U.S. Cl.
CPC ..... *G01N 33/6848* (2013.01); *G01N 33/6845* (2013.01); *G01N 2560/00* (2013.01)

(58) Field of Classification Search
CPC .......... G01N 33/6848; G01N 33/6845; G01N 2560/00; G01N 30/72; G01N 2030/8831; G01N 33/6854; G01N 2458/15; G01N 1/34; G01N 1/4044; G01N 1/405; G01N 30/00; B01D 59/44; B01D 15/26; B01D 15/00; B01D 15/3804; B01D 15/3809; C12M 1/343; C12Q 1/6872; G01M 3/202; Y10T 436/25125; Y10T 436/25375; C07K 1/32; C07K 1/22
USPC ................ 435/7.1; 436/173, 175, 177, 178; 530/413, 417
See application file for complete search history.

(56) References Cited

U.S. PATENT DOCUMENTS

2011/0244445 A1* 10/2011 Moritz ............... G01N 30/7233
                                                   435/7.1
2019/0169675 A1    6/2019 Graham

OTHER PUBLICATIONS

Antonioli et al.("Capturing and amplifying impurities from purified recombinant monoclonal antibodies via peptide library beads: A proteomic study". Proteomics 7 (2007): 1624-1633) (Year: 2007).*

(Continued)

*Primary Examiner* — Christopher L Chin
(74) *Attorney, Agent, or Firm* — Kramer Levin Naftalis & Frankel LLP

(57) ABSTRACT

The present application provides methods and systems to identify host cell protein (HCP) impurities in a sample containing high-abundance proteins. The HCP impurities can be enriched using interacting peptide ligands which have been attached to solid support. The HCP impurities can be eluted from the solid support using solution containing phase transfer surfactants. The isolated HCP impurities can be digested to generate components of the isolated HCP impurities which can subsequently be identified using a mass spectrometer.

20 Claims, 10 Drawing Sheets
(10 of 10 Drawing Sheet(s) Filed in Color)
Specification includes a Sequence Listing.

(56) References Cited

OTHER PUBLICATIONS

Altomare et al ("An in depth proteomic analysis based on ProteoMiner, affinity chromatography and nano-HPLC-MS/MS to explain the potential health benefits of bovine colostrum". Journal of Pharmaceutical and Biomedical Analysis 121 (2016): 297-306). (Year: 2016).*

Candiano et al.(Combinatorial peptide ligand libraries for urine proteome analysis: Investigation of different elution systems Electrophoresis 30 (2009): 2405-2411) (Year: 2009).*

Doneanu et al.("Enhanced Detection of Low-Abundance Host Cell Protein Impurities in High-Purity Monoclonal Antibodies Down to 1 ppm Using Ion Mobility Mass Spectrometry Coupled with Multidimensional Liquid Chromatography" Anal. Chem. 87 (2015): 10283 -10291). (Year: 2015).*

Sigma-Aldrich ("safety Data Sheet—Sodium dodecyl sulphate" Jun. 13, 2018) (Year: 2018).*

1. Tscheliessnig et al "Host cell protein analysis in therapeutic protein bioprocessing methods and applications" Biotechnol. J. 8 (2013): 655-670. (Year: 2013).*

3. Reisinger et al "A mass spectrometry-based approach to host cell protein identification and its application in a comparability exercise" Analytical Biochemistry 463 (2014) 1-6. (Year: 2014).*

4. Thulasiraman et al "Reduction of the concentration difference of proteins in biological liquids using a library of combinatorial ligands" Electrophoresis 26 (2005): 3561-3571. (Year: 2005).*

Chen I-Hsuan et al: "Improved host cell protein analysis in monoclonal antibody products through ProteoMiner", Analytical Biochemistry, Academic Press, Amsterdam, NL, vol. 610, Sep. 23, 2020 (Sep. 23, 2020).

Frederic Fortis et al: "A New Approach for the Detection and Identification of Protein Impurities Using Combinatorial Solid Phase Ligand Libraries", Journal of Proteome Research, vol. 5, No. 10, Oct. 1, 2006 (Oct. 1, 2006), pp. 2577-2585.

International Search Report, Application No. PCT/US2021/024919, Filing Date, Mar. 30, 2021, dated Jul. 5, 2021.

* cited by examiner

SEQUENCE LISTING

```
<160> NUMBER OF SEQ ID NOS: 2

<210> SEQ ID NO 1
<211> LENGTH: 16
<212> TYPE: PRT
<213> ORGANISM: Artificial Sequence
<220> FEATURE:
<223> OTHER INFORMATION: Poly-binding-splicing Factor PUF60

<400> SEQUENCE: 1

Ile Tyr Val Ala Ser Val His Gln Asp Leu Ser Asp Asp Asp Ile Lys
1               5                   10                  15

<210> SEQ ID NO 2
<211> LENGTH: 8
<212> TYPE: PRT
<213> ORGANISM: Artificial Sequence
<220> FEATURE:
<223> OTHER INFORMATION: Protein NipSnap homolog 3B

<400> SEQUENCE: 2

Thr Tyr Phe Leu Lys Pro Ser Lys
1               5
```

METHODS FOR CHARACTERIZING LOW-ABUNDANCE HOST CELL PROTEINS

FIELD

The present invention generally pertains to methods and systems for identifying and quantitating low-abundance host cell proteins (HCP) to monitor and control impurities in biopharmaceutical products.

SEQUENCE LISTING

The instant application contains a Sequence Listing which has been submitted electronically in ASCII format and is hereby incorporated by reference in its entirety. Said ASCII copy, created on May 31, 2023, is named 070816-01962 (10696US01) SL.txt and is 844 bytes in size.

BACKGROUND

Recombinant DNA technology has been used widely for producing biopharmaceutical products in host cells. Biopharmaceutical products must meet very high standards of purity. Thus, it can be important to monitor any impurities in such biopharmaceutical products at different stages of drug development, production, storage and handling. Residual impurities should be at an acceptable low level prior to conducting clinical studies. For example, host cell proteins (HCPs) can be present in protein-based biopharmaceuticals which are developed using cell-based systems. The presence of HCPs in drug products need to be monitored and can be unacceptable above a certain amount. Sometimes, even trace amounts of HCPs can cause an immunogenic response.

Immuno-assays have been used to monitor HCP removal using polyclonal anti-HCP antibodies. Immuno-assays can provide semi-quantitation of total HCPs levels in high throughput, but they may not be effective in quantitating individual HCPs rapidly. Liquid chromatography-mass spectrometry (LC-MS) has recently emerged for monitoring HCP removal. However, the enormous dynamic concentration ranges of HCPs in the presence of high concentration of purified antibodies can be a challenge for developing LC-MS method to monitor the removal of HCPs.

It will be appreciated that a need exists for methods and systems to identify and quantitate HCPs to monitor and control the residual HCPs in drug substance to mitigate safety risks.

SUMMARY

The identification of HCP impurities in biopharmaceutical products encounters challenges of dealing with the broad dynamic range of protein concentrations due to very high sample complexity. The present application provides methods and systems to identify HCP impurities in a sample containing high-abundance proteins including an enrichment method to fulfill the need of enriching low abundance HCPs in therapeutic drug products.

This disclosure provides a method of identifying and/or quantifying HCP impurities in a sample. In one exemplary embodiment, the method of identifying and/or quantifying HCP impurities in a sample comprises: contacting the sample to solid support, wherein interacting peptide ligands have been attached to the solid support and the HCP impurities can bind to the interacting peptide ligands; washing the solid support using a solution comprising a surfactant to isolate HCP impurities and provide an eluent; subjecting the eluent to an enzymatic digestion reaction to generate components of the isolated HCP impurities; and identifying the components of the isolated HCP impurities using a mass spectrometer; wherein the sample comprises at least one high-abundance peptide or protein. In one aspect, the surfactant in the method of the present application is a phase transfer surfactant, an ionic surfactant, an anionic surfactant, a cationic surfactant or combinations thereof. In another aspect, the surfactant in the method of the present application is sodium deoxycholate, sodium lauryl sulfate or sodium dodecylbenzene sulphonate.

In one aspect, a concentration of the at least one high-abundance peptide or protein in the method of the present application is about at least 1000 times, about 10,000 times, about 100,000 times or about 1,000,000 times higher than a concentration of the each HCP impurity. In one aspect, the interacting peptide ligands in the method of the present application are a library of combinatorial hexapeptide ligands. In another aspect, the HCP impurities in the method of the present application are quantified using a mass spectrometer, wherein a detection limit of each HCP impurity is about 0.05-0.1 ppm. In another aspect, the at least one high-abundance peptide or protein in the method of the present application is an antibody, a bispecific antibody, an antibody fragment, a Fab region of an antibody, an antibody-drug conjugate, a fusion protein, a protein pharmaceutical product or a drug. In one aspect, an enzyme of the enzymatic digestion reaction in the method of the present application is trypsin.

In yet another aspect, the mass spectrometer in the method of the present application is an electrospray ionization mass spectrometer, nano-electrospray ionization mass spectrometer or a triple quadrupole mass spectrometer, wherein the mass spectrometer is coupled to a liquid chromatography system. In one aspect, the mass spectrometer is capable of performing LC-MS (liquid chromatography-mass spectrometry) or a LC-MRM-MS (liquid chromatography-multiple reaction monitoring-mass spectrometry) analyses.

This disclosure, at least in part, provides a system for identifying HCP impurities in a sample. In one exemplary embodiment, the system for identifying HCP impurities in a sample comprises: a solid support; interacting peptide ligands, wherein the interacting peptide ligands are attached to the solid support such that the HCP impurities can bind to the interacting peptide ligands; a solution comprising a surfactant capable of washing the solid support to isolate HCP impurities; an enzymatic digestion solution capable of generating components from the isolated HCP impurities; and a mass spectrometer capable of identifying or quantifying the components from the isolated HCP impurities; wherein the sample comprises at least one high-abundance peptide or protein.

In one aspect, the surfactant in the system of the present application is a phase transfer surfactant, an ionic surfactant, an anionic surfactant, a cationic surfactant, or combinations thereof. In one aspect, the surfactant in the system of the present application is sodium deoxycholate, sodium lauryl sulfate, or sodium dodecylbenzene sulphonate. In another aspect, a concentration of the at least one high-abundance peptide or protein in the system of the present application is about at least 1000 times, about 10,000 times, about 100,000 times or about 1,000,000 times higher than a concentration of the each HCP impurity. In another aspect, the interacting peptide ligands in the system of the present application are a library of combinatorial hexapeptide ligands. In one aspect, a detection limit of each HCP impurity in the system of the present application is about 0.05-0.1 ppm. In yet another aspect, the at least one high-abundance peptide or protein in the system of the present application is an antibody, a bispecific antibody, an antibody fragment, a Fab region of an antibody, an antibody-drug conjugate, a fusion protein, a protein pharmaceutical product or a drug. In yet another aspect, an enzyme of the enzymatic digestion solution in the system of the present application is trypsin.

In one aspect, the mass spectrometer in the system of the present application is an electrospray ionization mass spectrometer, nano-electrospray ionization mass spectrometer, or a triple quadrupole mass spectrometer, wherein the mass spectrometer is coupled to a liquid chromatography system. In another aspect, the mass spectrometer in the system of the present application is capable of performing LC-MS or a LC-MRM-MS analyses.

These, and other, aspects of the invention will be better appreciated and understood when considered in conjunction with the following description and the accompanying drawings. The following description, while indicating various embodiments and numerous specific details thereof, is given by way of illustration and not of limitation. Many substitutions, modifications, additions, or rearrangements may be made within the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
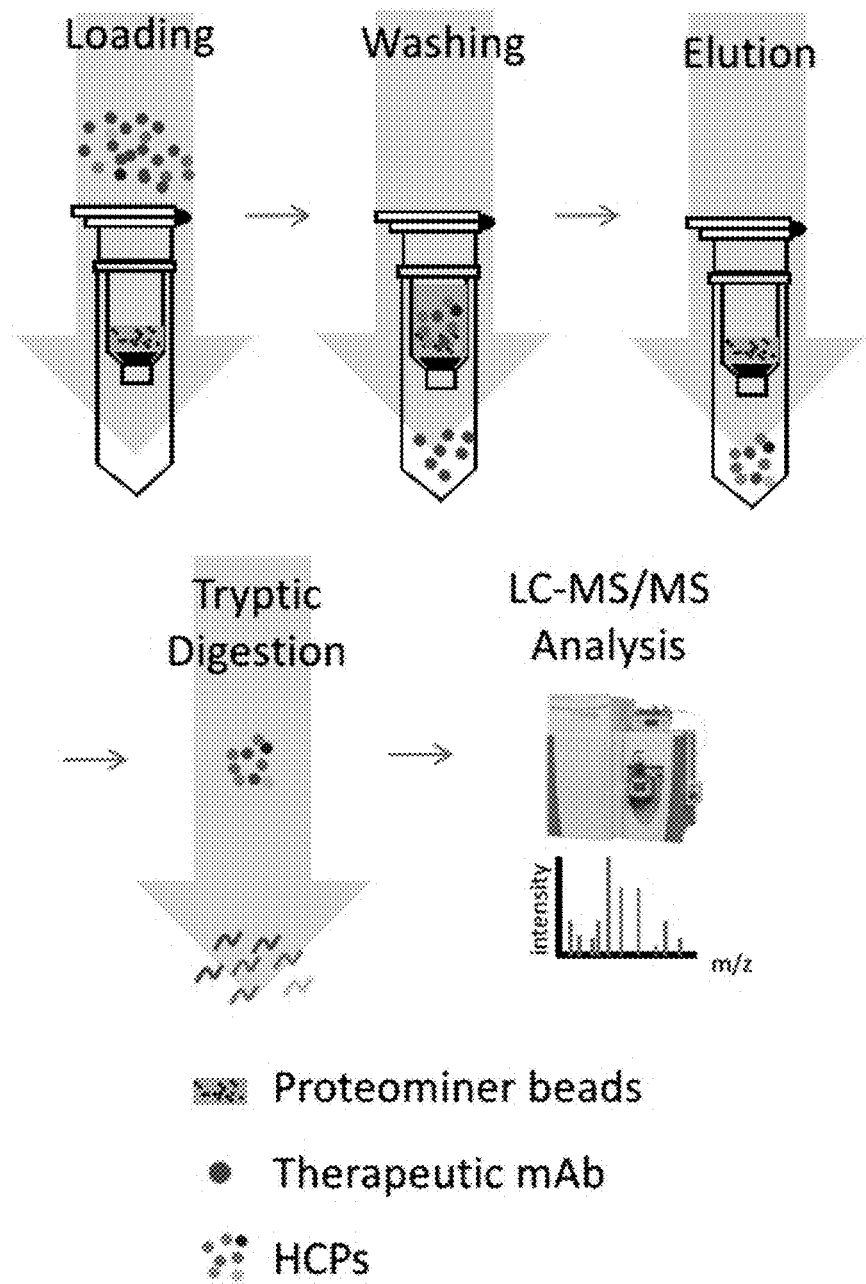
FIG. 1 shows a general workflow of using ProteoMiner™ beads to enrich HCPs including the steps of loading, washing, eluting, tryptic digesting and LC-MS/MS analysis according to an exemplary embodiment.

In order to manufacture biopharmaceutical products, it is important to obtain biopharmaceutical products having high purity, since residual HCPs can compromise product safety and stability. For producing cell-based recombinant therapeutic antibodies, typically, immuno-assays, such as enzyme-linked immunosorbent assays (ELISA), have been used to monitor HCP removal (clearance) using polyclonal anti-HCP antibodies during process development. ELISA can provide semi-quantitation of total HCPs levels in high throughput. However, since polyclonal anti-HCP antibodies are used for ELISA to capture, detect and quantify total HCPs, they may not be effective in quantitating individual HCPs. In particular, some non-immunogenic or weakly-immunogenic HCPs may not be detected using ELISA.

In order to both identify and quantify HCPs, several complementary approaches have been used to monitor HCPs, such as one-dimensional/two-dimensional (1D/2D) PAGE or liquid chromatography (LC) coupled tandem mass spectrometry (LC-MS/MS). However, the wide dynamic concentration ranges of HCPs in the presence of high concentration of purified antibodies may be a major challenge for developing LC-MS methods to monitor the removal of HCP impurities. Mass spectrometry (MS) alone lacks the capability to detect low abundance targets, such as low ppm levels of HCPs, in the presence of high concentrations of therapeutic antibodies due to the wide dynamic concentration ranges, which can be over six orders of magnitude. To overcome this issue, one strategy can be to resolve the co-eluting peptides before MS analysis by adding another dimension of separation, such as 2D-LC and/or ion mobility, in combination with the data-dependent acquisition or data-independent acquisition to increase the separation efficiency.

Huang et al. (Huang et al., A Novel Sample Preparation for Shotgun Proteomics Characterization of HCPs in Antibodies, Anal Chem. 2017, May 16; 89 (10):5436-5444) describes a sample preparation method using trypsin digestion for shotgun proteomics characterization of HCP impurities in an antibody sample. Huang's sample preparation method maintains the antibody nearly intact while HCPs are digested. Huang's approach can reduce the dynamic range for HCP detection using mass spectrometry by one to two orders of magnitude compared to traditional trypsin digestion sample preparation. As demonstrated by HCP spiking experiments, Huang's approach can detect 0.5 ppm of HCPs with molecular weight greater than 60 kDa, such as rPLBL2. For example, sixty mouse HCP impurities were detected in RM 8670 (NISTmAb, NIST monoclonal antibody standard, expressed in a murine cell line, obtained from the National Institute of Standards and Technology, Gaithersburg, MD) using Huang's approach.

Doneanu et al. (Doneanu et al., Enhanced Detection of Low-Abundance Host Cell Protein Impurities in High-Purity Monoclonal Antibodies Down to 1 ppm Using Ion Mobility Mass Spectrometry Coupled with Multidimensional Liquid Chromatography, Anal. Chem. 2015 Oct. 20; 87(20):10283-10291) reports the detection of low-abundance HCP impurities down to 1 ppm in antibody samples using liquid chromatography-mass spectrometry (LC-MS) methods. Doneanu's approach includes using a new charge-surface-modified C18 stationary phase to mitigate the challenges of column saturation, incorporating traveling-wave ion mobility separation of co-eluting peptide precursors, and improving fragmentation efficiency of low-abundance HCP peptides by correlating the collision energy used for precursor fragmentation with the mobility drift time. The identification of HCP impurities can be detected at 10-50 ppm using 2D-HPLC (2D-High Performance Liquid Chromatography) in combination with ion mobility mass spectrometry analysis. However, the cycle times for 2D-LC or 2D-HPLC can be very long. In addition, these methods may not be sensitive enough for low level HCP analysis, such as less than 10 ppm. Other approaches of identifying HCP impurities include sample preparations to enrich HCPs by removing antibodies in the sample, such as using affinity purification or limited digestion to remove antibodies. In addition, using polyclonal antibodies to capture HCPs is another common approach.

Analytical techniques required for identifying HCP impurities encounter the challenges of dealing with about 1 million times more matrix molecules than the analytes, for example, HCPs or HCP peptides, due to very high sample complexity. Exploration of HCP enrichment to reach levels of detection is not easy to implement, since HCP impurities are most often present at low levels, such as 1-100 ppm, in protein biopharmaceuticals. Without knowing the identities and properties of HCPs, it can be very challenging to develop a general sample preparation procedure to enrich HCPs (or HCP peptides) or remove the matrix background (Doneanu et al.).

The present application provides a method to enrich HCPs using interacting peptide ligands, such as a combinatorial ligand library. In some exemplary embodiments, ProteoMiner™ beads (Bio-Rad Laboratories, Inc., Hercules, CA), for example, a combinatorial hexapeptide library immobilized on beads, are used to enrich HCPs. When the peptide-ligand conjugated beads are applied to a sample containing various protein species, each protein species can bind to its interacting peptide ligands. HCPs bind to their interacting peptide ligands mainly by hydrophobic force in combination with some weak interaction forces, such as ionic interaction and hydrogen bonding.

A protein species which is high abundance can saturate its interacting peptide ligands due to the presence of excess quantity, since there are limited numbers of interacting peptide ligands corresponding to each protein species in the combinatorial ligand library. The limited numbers of corresponding interacting peptide ligands can be saturated easily in the presence of excess quantity of high-abundance proteins. The excess quantity of high-abundance proteins which are unable to bind to the interacting peptide ligands can be washed off from the beads. Since the quantity of low-abundance proteins in the sample is relatively low in comparison to the high-abundance proteins, the low-abundance proteins may not saturate their corresponding interacting peptide ligands. Therefore, the low-abundance proteins can be relatively enriched in comparison to the high-abundance proteins. After conducting the enrichment process, the broad dynamic range of protein concentrations can be significantly reduced to allow detection of low abundance proteins. The HCP enrichment method of the present application can enrich and detect mid-abundance and low-abundance proteins by decreasing the quantity of high-abundance proteins. The HCP enrichment method of the present application also fulfills the need of enriching low abundance HCP impurities in therapeutic drug product.

In some exemplary embodiments, antibody samples are treated with ProteoMiner™ beads to reduce the quantity of antibodies which are present in high abundance and to enrich low abundance HCP impurities. The HCP-enriched sample is subsequently subjected to shotgun proteomic analysis. This procedure can enrich the low abundance HCP impurities and reduce the levels of antibody at the same time. It can successfully reduce the dynamic concentration ranges among HCPs and antibody drugs allowing for the detection of low abundance HCP impurities. The detection limit of the HCP impurities using the HCP enrichment method of the present application is about 0.05-0.1 ppm.

In some exemplary embodiments, the present application provides a method of identifying host cell protein (HCP) impurities in a sample, comprising: contacting the sample to solid supports, wherein interacting peptide ligands have been attached to the solid supports and the HCP impurities can bind to the interacting peptide ligands; washing the solid supports using a solution comprising a surfactant to isolate HCP impurities to provide an eluent; subejcting the eluent with an enzymatic digestion reaction to generate components of the isolated HCP impurities; and identifying the components of the isolated HCP impurities using a mass spectrometer; wherein the sample comprises at least one high-abundance peptide or protein.

In some exemplary embodiments, phase transfer surfactants (PTS), such as sodium deoxycholate (SDC) and sodium lauryl sulfate (SLS), are used to elute HCPs from ProteoMiner™ beads. SDC is an ionic detergent that is especially useful for disrupting and dissociating protein interactions. Ionic detergents have a hydrophilic head group that is charged and can be either negatively (anionic) or positively (cationic) charged. SLS is an anionic surfactant. Anionic detergents, such as SLS or sodium dodecylbenzene sulphonate, are sodium salts of sulphonated long chain, alcohols or hydrocarbons.

In some exemplary embodiments, the elution buffer to elute HCPs from ProteoMiner™ beads contains ionic, anionic, cationic, phase transfer surfactants, or combinations thereof. In one aspect, the elution buffer contains SDC, SLS, or sodium dodecylbenzene sulphonate. In one aspect, the elution buffer comprises PTS buffer containing 12 mM SDC (sodium deoxycholate), 12 mM SLS (sodium lauroyl sarcosinate), 10 mM TCEP (Tris(2-carboxyethyl)phosphine, a reducing agent) and 30 mM CAA (chloroacetamide).

Trace amounts of particular HCPs may cause immune response or toxic biologic activities after drug injection. The presence of residual HCPs in biopharmaceutical products has been a concern for drug safety which has led to an increasing demand for developing methods and systems to identify and characterize HCP impurities in biopharmaceutical products. There are unmet needs to identify and monitor individual HCPs for risk assessment of the presence of HCPs in therapeutic protein products.

This disclosure provides methods and systems to satisfy the aforementioned demands by providing methods and systems to identify and quantitate HCPs to monitor and control the residual HCPs in drug substance to mitigate safety risks. Exemplary embodiments disclosed herein satisfy the aforementioned demands and the long felts needs.

The term "a" should be understood to mean "at least one"; and the terms "about" and "approximately" should be understood to permit standard variation as would be understood by those of ordinary skill in the art; and where ranges are provided, endpoints are included.

As used herein, the terms "include," "includes," and "including," are meant to be non-limiting and are understood to mean "comprise," "comprises," and "comprising," respectively.

In some exemplary embodiments, the present application provides a method of identifying host cell protein (HCP) impurities in a sample, comprising: contacting the sample to solid support, wherein interacting peptide ligands have been attached to the solid support and wherein the HCP impurities can bind to the interacting peptide ligands; washing the solid support using a solution comprising a surfactant to isolate HCP impurities to provide an eluent; subjecting the eluent with an enzymatic digestion reaction to generate components of the isolated HCP impurities; and identifying the components of the isolated HCP impurities using a mass spectrometer; wherein the sample comprises at least one high-abundance peptide or protein.

As used herein, the term "peptide" or "protein" includes any amino acid polymer having covalently linked amide bonds. Proteins comprise one or more amino acid polymer chains, generally known in the art as "peptide" or "polypeptides". A protein may contain one or multiple polypeptides to form a single functioning biomolecule. In some exemplary embodiments, the protein can be an antibody, a bispecific antibody, a multi-specific antibody, antibody fragment, monoclonal antibody, host-cell protein or combinations thereof.

In one aspect, the at least one high-abundance peptide or protein in the method of the present application is an antibody, a bispecific antibody, an antibody fragment, a Fab region of an antibody, an antibody-drug conjugate, a fusion protein, a protein pharmaceutical product, or a drug. In on aspect, the high-abundance protein is VEGF-Trap (examples of which are disclosed in U.S. Pat. No. 7,279,159). In a preferred aspect, the high-abundance protein is aflibercept.

As used herein, an "antibody" is intended to refer to immunoglobulin molecules consisting of four polypeptide chains, two heavy (H) chains and two light (L) chains inter-connected by disulfide bonds. Each heavy chain has a heavy chain variable region (HCVR or VH) and a heavy chain constant region. The heavy chain constant region contains three domains, CH1, CH2 and CH3. Each light chain has of a light chain variable region and a light chain constant region. The light chain constant region consists of one domain (CL). The VH and VL regions can be further subdivided into regions of hypervariability, termed complementarity determining regions (CDR), interspersed with regions that are more conserved, termed framework regions (FR). Each VH and VL can be composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" is inclusive of, but not limited to, those that are prepared, expressed, created or isolated by recombinant means, such as antibodies isolated from a host cell transfected to express the antibody. An IgG comprises a subset of antibodies.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, for example, from full antibody molecules using any suitable standard techniques such as proteolytic digestion or recombinant genetic engineering techniques involving the manipulation and expression of DNA encoding antibody variable and optionally constant domains. Such DNA is known and/or is readily available from, for example, commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

As used herein, an "antibody fragment" includes a portion of an intact antibody, such as, for example, the antigen-binding or variable region of an antibody. Examples of antibody fragments include, but are not limited to, a Fab fragment, a Fab' fragment, a F(ab')2 fragment, a scFv fragment, a Fv fragment, a dsFv diabody, a dAb fragment, a Fd' fragment, a Fd fragment, and an isolated complementarity determining region (CDR) region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. In some exemplary embodiments, an antibody fragment contains sufficient amino acid sequence of the parent antibody of which it is a fragment that it binds to the same antigen as does the parent antibody; in some exemplary embodiments, a fragment binds to the antigen with a comparable affinity to that of the parent antibody and/or competes with the parent antibody for binding to the antigen. An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains that are linked together, for example, by disulfide linkages. An antibody fragment may optionally comprise a multi-molecular complex. A functional antibody fragment typically comprises at least about 50 amino acids and more typically comprises at least about 200 amino acids.

The phrase "bispecific antibody" includes an antibody capable of selectively binding two or more epitopes. Bispecific antibodies generally comprise two different heavy chains, with each heavy chain specifically binding a different epitope—either on two different molecules (e.g., antigens) or on the same molecule (e.g., on the same antigen). If a bispecific antibody is capable of selectively binding two different epitopes (a first epitope and a second epitope), the affinity of the first heavy chain for the first epitope will generally be at least one to two or three or four orders of magnitude lower than the affinity of the first heavy chain for the second epitope, and vice versa. The epitopes recognized by the bispecific antibody can be on the same or a different target (e.g., on the same or a different protein). Bispecific antibodies can be made, for example, by combining heavy chains that recognize different epitopes of the same antigen. For example, nucleic acid sequences encoding heavy chain variable sequences that recognize different epitopes of the same antigen can be fused to nucleic acid sequences encoding different heavy chain constant regions, and such sequences can be expressed in a cell that expresses an immunoglobulin light chain.

A typical bispecific antibody has two heavy chains each having three heavy chain CDRs, followed by a CH1 domain, a hinge, a CH2 domain, and a CH3 domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding or one or both of the heavy chains to one or both epitopes. BsAbs can be divided into two major classes, those bearing an Fc region (IgG-like) and those lacking an Fc region, the latter normally being smaller than the IgG and IgG-like bispecific molecules comprising an Fc. The IgG-like bsAbs can have different formats, such as, but not limited to triomab, knobs into holes IgG (kih IgG), crossMab, orth-Fab IgG, Dual-variable domains Ig (DVD-Ig), Two-in-one or dual action Fab (DAF), IgG-single-chain Fv (IgG-scFv), or κλ-bodies. The non-IgG-like different formats include Tandem scFvs, Diabody format, Single-chain diabody, tandem diabodies (Tand-Abs), Dual-affinity retargeting molecule (DART), DART-Fc, nanobodies, or antibodies produced by the dock-and-lock (DNL) method (Gaowei Fan, Zujian Wang & Mingju Hao, *Bispecific antibodies and their applications*, 8 JOURNAL OF HEMATOLOGY & ONCOLOGY 130; Dafne Müller & Roland E. Kontermann, *Bispecific Antibodies*, HANDBOOK OF THERAPEUTIC ANTIBODIES 265-310 (2014)).

The methods of producing BsAbs are not limited to quadroma technology based on the somatic fusion of two different hybridoma cell lines, chemical conjugation, which involves chemical cross-linkers, and genetic approaches utilizing recombinant DNA technology. Examples of bsAbs include those disclosed in the following patent applications, which are hereby incorporated by reference: U.S. Ser. No. 12/823,838, filed Jun. 25, 2010; U.S. Ser. No. 13/488,628, filed Jun. 5, 2012; U.S. Ser. No. 14/031,075, filed Sep. 19, 2013; U.S. Ser. No. 14/808,171, filed Jul. 24, 2015; U.S. Ser. No. 15/713,574, filed Sep. 22, 2017; U.S. Ser. No. 15/713, 569, field Sep. 22, 2017; U.S. Ser. No. 15/386,453, filed Dec. 21, 2016; U.S. Ser. No. 15/386,443, filed Dec. 21, 2016; U.S. Ser. No. 15/22343 filed Jul. 29, 2016; and U.S. Ser. No. 15/814,095, filed Nov. 15, 2017. Low levels of homodimer impurities can be present at several steps during the manufacturing of bispecific antibodies. The detection of such homodimer impurities can be challenging when performed using intact mass analysis due to low abundances of the homodimer impurities and the co-elution of these impurities with main species when carried out using a regular liquid chromatographic method.

As used herein "multispecific antibody" or "Mab" refers to an antibody with binding specificities for at least two different antigens. While such molecules normally will only bind two antigens (e.g., bispecific antibodies, BsAbs), antibodies with additional specificities such as trispecific antibody and KIH Trispecific can also be addressed by the system and method disclosed herein.

The term "monoclonal antibody" as used herein is not limited to antibodies produced through hybridoma technology. A monoclonal antibody can be derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof.

In some exemplary embodiments, the protein can be purified from mammalian cells. The mammalian cells can be of human origin or non-human origin can include primary epithelial cells (e.g., keratinocytes, cervical epithelial cells, bronchial epithelial cells, tracheal epithelial cells, kidney epithelial cells and retinal epithelial cells), established cell lines and their strains (e.g., 293 embryonic kidney cells, BHK cells, HeLa cervical epithelial cells and PER-C6 retinal cells, MDBK (NBL-1) cells, 911 cells, CRFK cells, MDCK cells, CHO cells, BeWo cells, Chang cells, Detroit 562 cells, HeLa 229 cells, HeLa S3 cells, Hep-2 cells, KB cells, LSI80 cells, LS174T cells, NCI-H-548 cells, RPMI2650 cells, SW-13 cells, T24 cells, WI-28 VA13, 2RA cells, WISH cells, BS-C-I cells, LLC-MK2 cells, Clone M-3 cells, 1-10 cells, RAG cells, TCMK-1 cells, Y-1 cells, LLC-PKi cells, PK(15) cells, GHi cells, GH3 cells, L2 cells, LLC-RC 256 cells, MHiCi cells, XC cells, MDOK cells, VSW cells, and TH-I, B1 cells, BSC-1 cells, RAf cells, RK-cells, PK-15 cells or derivatives thereof), fibroblast cells from any tissue or organ (including but not limited to heart, liver, kidney, colon, intestines, esophagus, stomach, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., CHO cells, TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, Midi cells, CHO cells, CV-1 cells, COS-1 cells, COS-3 cells, COS-7 cells, Vero cells, DBS-FrhL-2 cells, BALB/3T3 cells, F9 cells, SV-T2 cells, M-MSV-BALB/3T3 cells, K-BALB cells, BLO-11 cells, NOR-10 cells, C3H/IOTI/2 cells, HSDMiC3 cells, KLN205 cells, McCoy cells, Mouse L cells, Strain 2071 (Mouse L) cells, L-M strain (Mouse L) cells, L-MTK' (Mouse L) cells, NCTC clones 2472 and 2555, SCC-PSA1 cells, Swiss/3T3 cells, Indian muntjac cells, SIRC cells, Cn cells, and Jensen cells, Sp2/0, NS0, NS1 cells or derivatives thereof).

As used herein, the term "host-cell protein" includes protein derived from the host cell and can be unrelated to the desired protein of interest. Host-cell protein can be a process-related impurity which can be derived from the manufacturing process and can include the three major categories: cell substrate-derived, cell culture-derived and downstream derived. Cell substrate-derived impurities include, but are not limited to, proteins derived from the host organism and nucleic acid (host cell genomic, vector, or total DNA). Cell culture-derived impurities include, but are not limited to, inducers, antibiotics, serum, and other media components. Downstream-derived impurities include, but are not limited to, enzymes, chemical and biochemical processing reagents (e.g., cyanogen bromide, guanidine, oxidizing and reducing agents), inorganic salts (e.g., heavy metals, arsenic, nonmetallic ion), solvents, carriers, ligands (e.g., monoclonal antibodies), and other leachables.

In some exemplary embodiments, the host-cell protein can have a pI in the range of about 4.5 to about 9.0. In one exemplary specific embodiment, the pI can be about 4.5, about 5.0, about 5.5, about 5.6, about 5.7, about 5.8, about 5.9, about 6.0, about 6.1 about 6.2, about 6.3, about 6.4, about 6.5, about 6.6, about 6.7, about 6.8, about 6.9, about 7.0, about 7.1 about 7.2, about 7.3, about 7.4, about 7.5, about 7.6, about 7.7, about 7.8, about 7.9, about 8.0, about 8.1 about 8.2, about 8.3, about 8.4, about 8.5, about 8.6, about 8.7, about 8.8, about 8.9, or about 9.0.

In some exemplary embodiments, the types of host-cell proteins in the composition can be at least two.

As used herein, a "protein pharmaceutical product" or "biopharmaceutical product" includes an active ingredient which can be fully or partially biological in nature. In one aspect, the protein pharmaceutical product can comprise a peptide, a protein, a fusion protein, an antibody, an antigen, vaccine, a peptide-drug conjugate, an antibody-drug conjugate, a protein-drug conjugate, cells, tissues, or combinations thereof. In another aspect, the protein pharmaceutical product can comprise a recombinant, engineered, modified, mutated, or truncated version of a peptide, a protein, a fusion protein, an antibody, an antigen, vaccine, a peptide-drug conjugate, an antibody-drug conjugate, a protein-drug conjugate, cells, tissues, or combinations thereof.

In another exemplary embodiment, the sample can be obtained from any step of the bioprocess, such as, culture cell culture fluid (CCF), harvested cell culture fluid (HCCF), process performance qualification (PPQ), any step in the downstream processing, drug solution (DS), or a drug product (DP) comprising the final formulated product. In some other specific exemplary embodiments, the sample can be selected from any step of the downstream process of clarification, chromatographic purification, viral inactivation, or filtration. In some specific exemplary embodiments, the drug product can be selected from manufactured drug product in the clinic, shipping, storage, or handling.

As used herein, a "mass spectrometer" includes a device capable of identifying specific molecular species (or components as referred to herein) and measuring their accurate masses. The term is meant to include any molecular detector into which a polypeptide or peptide may be eluted for detection and/or characterization. A mass spectrometer can include three major parts: the ion source, the mass analyzer, and the detector. The role of the ion source is to create gas phase ions. Analyte atoms, molecules, or clusters can be transferred into gas phase and ionized either concurrently (as in electrospray ionization). The choice of ion source depends heavily on the application In one aspect, the mass spectrometer in the method of the present application is an electrospray ionization mass spectrometer, nano-electrospray ionization mass spectrometer, or a triple quadrupole mass spectrometer, wherein the mass spectrometer is coupled to a liquid chromatography system.

As used herein, the term "electrospray ionization" or "ESI" refers to the process of spray ionization in which either cations or anions in solution are transferred to the gas phase via formation and desolvation at atmospheric pressure of a stream of highly charged droplets that result from applying a potential difference between the tip of the electrospray needle containing the solution and a counter electrode. There are generally three major steps in the production of gas-phase ions from electrolyte ions in solution. These are: (a) production of charged droplets at the ES infusion tip; (b) shrinkage of charged droplets by solvent evaporation and repeated droplet disintegrations leading to small highly charged droplets capable of producing gas-phase ions; and (c) the mechanism by which gas-phase ions are produced from very small and highly charged droplets. Stages (a)-(c) generally occur in the atmospheric pressure region of the apparatus. In some exemplary embodiments, the electrospray ionization mass spectrometer can be a nano-electrospray ionization mass spectrometer.

As used herein, the term "triple quadruple mass spectrometer" refers to a tandem mass spectrometer consisting of two quadrupole mass analyzers in series, with a (non-mass-resolving) radio frequency (RF), only quadrupole between them to act as a cell for collision-induced dissociation. In a triple quadrupole mass spectrometer, a peptide sample is injected onto an LC coupled with a MS instrument. The first quadrupole can be used as a mass filter to isolate peptides with a targeted m/z. The second quadrupole serves as a collision cell to break the peptide into fragments. The third quadrupole serves as a second mass filter for specified m/z fragments from the initial parent peptide. As used herein, the term "tandem mass spectrometry" includes a technique where structural information on sample molecules can be obtained by using multiple stages of mass selection and mass separation. A prerequisite is that the sample molecules can be transferred into gas phase and ionized intact and that they can be induced to fall apart in some predictable and controllable fashion after the first mass selection step. Multistage MS/MS, or $MS^n$, can be performed by first selecting and isolating a precursor ion ($MS^2$), fragmenting it, isolating a primary fragment ion ($MS^3$), fragmenting it, isolating a secondary fragment ($MS^4$), and so on as long as one can obtain meaningful information or the fragment ion signal can be detectable. Tandem MS have been successfully performed with a wide variety of analyzer combinations. The analyzers to combine for a certain application can be determined by many different factors, such as sensitivity, selectivity, and speed, but also size, cost, and availability. The two major categories of tandem MS methods are tandem-in-space and tandem-in-time, but there are also hybrids where tandem-in-time analyzers are coupled in space or with tandem-in-space analyzers. A tandem-in-space mass spectrometer comprises an ion source, a precursor ion activation device, and at least two non-trapping mass analyzers. Specific m/z separation functions can be designed so that in one section of the instrument ions are selected, dissociated in an intermediate region, and the product ions are then transmitted to another analyzer for m/z separation and data acquisition. In tandem-in-time mass spectrometer ions produced in the ion source can be trapped, isolated, fragmented, and m/z separated in the same physical device.

The peptides identified by the mass spectrometer can be used as surrogate representatives of the intact protein and their post translational modifications. They can be used for protein characterization by correlating experimental and theoretical MS/MS data, the latter generated from possible peptides in a protein sequence database. The characterization includes, but is not limited, to sequencing amino acids of the protein fragments, determining protein sequencing, determining protein de novo sequencing, locating post-translational modifications, or identifying post translational modifications, or comparability analysis, or combinations thereof.

As used herein, the term "database" refers to bioinformatic tools which provide the possibility of searching the uninterpreted MS-MS spectra against all possible sequences (or components as referred to herein) in the database(s). Non-limiting examples of such tools are Mascot (http://www.matrixscience.com), Spectrum Mill (http://www.chem.agilent.com), PLGS (http://www.waters.com), PEAKS (http://www.bioinformaticssolutions.com), Proteinpilot (http://download.appliedbiosystems.com//proteinpilot), Phenyx (http://www.phenyx-ms.com), Sorcerer (http://www.sagenresearch.com), OMS SA (http://www.pubchem.ncbi.nlm.nih.gov/omssa/), X!Tandem (http://www.thegpm.org/TANDEM/), Protein Prospector (http:// www. http://prospector.ucsfedu/prospector/mshome.htm), Byonic (https://www.proteinmetrics.com/products/byonic) or Sequest (http://fields.scripps.edu/sequest).

In some exemplary embodiments, the mass spectrometer can be coupled to a liquid chromatography system.

As used herein, the term "liquid chromatography" refers to a process in which a chemical mixture carried by a liquid or gas can be separated into components as a result of differential distribution of the chemical entities as they flow around or over a stationary liquid or solid phase. Non-limiting examples of chromatography include traditional reversed-phased (RP), ion exchange (IEX), mixed mode chromatography and normal phase chromatography (NP).

Exemplary Embodiments

Embodiments disclosed herein provide methods and systems for identifying low-abundance HCP impurities in a sample.

In some exemplary embodiments, the present application provides a method of identifying host cell protein (HCP) impurities in a sample, comprising: contacting the sample to solid support, wherein interacting peptide ligands have been attached to the solid support and wherein the HCP impurities can bind to the interacting peptide ligands; washing the solid support using a solution comprising a surfactant to provide an eluent; subjecting the eluent to an enzymatic digestion reaction to generate components of the isolated HCP impurities; and identifying the components of the isolated HCP impurities using a mass spectrometer; wherein the sample comprises at least one high-abundance peptide or protein In one aspect, the solid support in the method or system of the present application can be beads, magnetic beads, chromatography resins, polymer, or chromatography matrix.

In one aspect, the surfactant in the method of the present application is a phase transfer surfactant, an ionic surfactant, an anionic surfactant, a cationic surfactant, or combinations thereof. In some aspects, the surfactant in the method of the present application is sodium deoxycholate, sodium lauryl sulfate, or sodium dodecylbenzene sulphonate.

In one aspect, a concentration of the at least one high-abundance peptide or protein in the method of the present application is about at least 5 times, about at least 100 times, about at least 1000 times, about 10,000 times, about 100,000 times or about 1,000,000 times higher than a concentration of the each HCP impurity. In one aspect, the HCP impurities in the method of the present application are quantified using a mass spectrometer, wherein a detection limit of the each HCP impurity is about 0.05-0.1 ppm, about 0.01-0.5 ppm, about 0.02-0.5 ppm, about 0.03-0.5 ppm, about 0.04-0.5 ppm, about 0.02-0.4 ppm, about 0.03-0.4 ppm, about 0.04-0.4 ppm, about 0.02-0.3 ppm, about 0.03-0.3 ppm, about 0.04-0.3 ppm, about 0.02-0.2 ppm, about 0.03-0.2 ppm or about 0.04-0.2 ppm.

It is understood that the system is not limited to any of the aforesaid HCPs, interacting peptide ligands, solid supports, biopharmaceutical products, peptides, proteins, antibodies, surfactants, protein pharmaceutical products, or mass spectrometer.

The consecutive labeling of method steps as provided herein with numbers and/or letters is not meant to limit the method or any embodiments thereof to the particular indicated order.

Various publications, including patents, patent applications, published patent applications, accession numbers, technical articles and scholarly articles are cited throughout the specification. Each of these cited references is incorporated by reference herein in its entirety and for all purposes. Unless described otherwise, all technical and scientific terms used herein have the same meaning as commonly understood by one of ordinary skill in the art to which this invention belongs.

This disclosure will be more fully understood by reference to the following Examples, which are provided to describe this disclosure in greater detail. They are intended to illustrate and should not be construed as limiting the scope of this disclosure.

EXAMPLES

Material and Methods
1. Material

ProteoMiner™ Protein Enrichment kit was purchased from Bio-Rad Laboratories, Inc. (Hercules, CA). ProteoMiner™ technology is a sample preparation tool for the compression of the dynamic range of protein concentration in biological samples. A large library of combinatorial hexapeptide ligands were immobilized on beads for capturing various proteins. ProteoMiner™ spin column contained 500 µl bead slurry (4% beads, 20% v/v aqueous EtOH) with 20 µl settled bead volume. The wash buffer of the kit contains 50 mL PBS (phosphate-buffer saline, 150 mM NaCl, 10 mN $NaH_2PO_4$, pH 7.4). The elution buffer of the kit contains lyophilized urea CHAPS (8 M urea, 2% CHAPS; CHAPS detergent is 3-((3-cholamidopropyl) dimethylammonio)-1-propanesulfonate). The rehydration buffer of the kit contains 5% acetic acid.

Chromatography solvents which were LC-MS grade were purchased from Thermo Fisher Scientific (Waltham, MA). Monoclonal antibodies were produced by Regeneron (Tarrytown, NY). CHO (Chinese hamster ovary) proteins which were spiked-in as HCPs were produced by Regeneron (Tarrytown, NY). Sodium deoxycholate (SDC), sodium lauroyl sarcosinate (SLS) and chloroacetamide (CAA) were purchased from Sigma-Aldrich (St. Louis, MO). Tris-(2-carboxyethyl) phosphine (TCEP) was purchased from Thermo Fisher Scientific. RM 8670 (NISTmAb, NIST monoclonal antibody standard, expressed in a murine cell line) was obtained from the National Institute of Standards and Technology (NIST, Gaithersburg, MD).

2. Protein Enrichments Using ProteoMiner™ Protein Enrichment Kit

ProteoMiner™ Protein Enrichment kit was used to enrich proteins in samples. A small-scale of ProteoMiner™ cartridge was used for five experiments. ProteoMiner™ beads were washed twice with 200 µL of washing buffer provided in the kit. The beads were resuspended with 200 µL of water and 40 µL of beads slurry was transferred to a tube for conducting one experiment. 8 mg NISTmAb, 15 mg mAb1 or 15 mg mAb2 was diluted to 50 mg/mL with water followed by adjusting pH of the solution to pH 6 using 25 mM pH 4.0 sodium acetate. The sample was added to ProteoMiner™ bead slurry for incubation at room temperature with rotation for 2 hrs. The sample mixture was then loaded into a tip with frit. The supernatant was removed by centrifuging at 1000×g for 1 minute. Subsequently, the beads were washed by adding 100 µL washing buffer into tip followed by centrifugation at 200×g for 1 minute three times. Finally, the enriched proteins were eluted using 10 µL of PTS buffer (12 mM SDC, 12 mM SLS, 10 mM TCEP and 30 mM CAA) followed by centrifugation at 200×g for 1 minute for three times. The collected eluent containing the enriched proteins was denatured, reduced and alkylated at 95° C. for 5 minutes. Alkylated proteins were diluted to 150

μL and digested with 1 of trypsin at 37° C. overnight to obtain a solution containing a peptide mixture. The solution containing the peptide mixture was acidified using 10 μL of 10% TFA to precipitate SDC and SLS. Subsequently, the solution containing the peptide mixture was centrifuged at 13,200 rpm for 5 minutes. The supernatant containing the peptide mixture was then desalted using GL-Tip GC desalting tip, and dried using SpeedVac.

3. Direct Digestion of NISTmAb

NIST monoclonal antibody standard, for example, NISTmAb, was digested with trypsin as reference material with the following procedures: 20 μg of NISTmAb (RM8670) was dried using a SpeedVac followed by reconstitution with 20 μL of PTS buffer; the antibodies (proteins) were denatured, reduced and alkylated at 95° C. for 5 minutes; alkylated proteins were diluted to 100 μL and digested with 1 μg of trypsin at 37° C. overnight to obtain a solution containing peptide mixture; the solution containing peptide mixture was acidified using 10 μL of 10% TFA to precipitate SDC and SLS in acidic condition, followed by centrifugation at 13,200 rpm for 5 minutes; the supernatant containing peptide mixture was then desalted using GL-Tip GC desalting tip followed by drying using SpeedVac; the dried peptide mixture was resuspended in 40 μL of 0.1% FA; and 2 μL resuspended solution was used for direct injection for LC-MS/MS analysis and PRM analysis.

4. LC-MS/MS Analysis

The desalted peptide mixture obtained from ProteoMiner™ enrichment was dried and resuspended in 40 μL of 0.1% formic acid (FA) solution. 5 μL of the solution containing the peptide mixture was injected into a low flow liquid chromatography system, for example, UltiMate™ 3000 RSLCnano system (Thermo Fisher Scientific) coupled to a Q-Exactive HFX mass spectrometer (Thermo Fisher Scientific). Peptides were separated on a 25 cm C18 column (inner diameter 0.075 mm, 2.0 μm, 100 Å, Thermo Fisher Scientific). The mobile phase buffer contained 0.1% FA in ultra-pure water (Buffer A) and the elution buffer contained 0.1% FA in 80% acetonitrile (ACN) (Buffer B). Peptides were eluted using a 100-minute linear gradient from 2-25% Buffer B at a flow rate of 300 nL/minute. The mass spectrometer was operated in data-dependent mode. The ten most intense ions were subjected to higher-energy collisional dissociation (HCD) fragmentation with the normalized collision energy (NCE) at 27% for each full MS scan at 120,000 resolution (automatic gain control (AGC) target 3e6, 60 ms maximum injection time, m/z 375-1500), and MS/MS events at 30,000 resolution (AGC target 1e5, 60 ms maximum injection time, m/z 200-2000). The MS proteomic data were deposited to the ProteomeXchange Consortium with project accession no. PXD016194 via JPOST repository.

5. PRM Analysis

1 μg of direct digested NISTmAb sample were injected into an UltiMate™ 3000 RSLCnano system coupled to a Q-Exactive HFX mass spectrometer. The digested peptides were separated using a 25 cm C18 column with an inner diameter of 0.075 mm (2.0 μm, 100 Å). The mobile phase buffer contained 0.1% FA in water (Buffer A) and the elution buffer contained 0.1% FA in 80% ACN (Buffer B). Peptides were eluted using a 100-minute linear gradient of 2-25% Buffer B at a flow rate of 300 nL/minute. Eluent from the column was introduced into the mass spectrometer through an emitter spray tip. Each sample was analyzed under parallel reaction monitoring (PRM) with an isolation window of 2 m/z. In all experiments, a full mass spectrum at 120,000 resolution relative to m/z 200 (AGC target 1e6, 60 ms maximum injection time, m/z 350-2000) was followed by time-scheduled PRM scans at 30,000 resolution (AGC target 1e5, 100 ms maximum injection time). HCD was used with 27% NCE.

Example 1. Enrichment of HCPs Using Various Elution Buffers

ProteoMiner™ beads were used to enrich HCPs in a sample containing antibodies and HCPs. The general workflow of using ProteoMiner™ beads to enrich HCPs included the steps of loading, washing, elution, tryptic digestion and LC-MS/MS analysis as shown in FIG. 1. Several buffers were tested to elute proteins from ProteoMiner™ beads including ProteoMiner™ elution buffer and several MS-compatible elution buffers, for example, PTS buffer, 8M urea in 5% acetic acid (AA), 6M guanidine and 0.1% TFA in 50% CAN (0.1% TFA/50% ACN). The elution buffer provided in ProteoMiner™ Protein Enrichment kit contained 2% CHAPS which was designed for compatibility of 1D/2D gel analysis. Since CHAPS is not compatible with mass spectrometry (MS) analysis, acetone precipitation or FASP (Filter-Aided Sample preparation) was tested to remove CHAPS from the eluent. FASP is a method utilizing disposable centrifugal ultrafiltration units for detergent depletion and protein digestion. Consecutive protein digestion was conducted using two or three proteases to enable generation of peptide fractions.

A sample containing mAb1 (10 mg) and HCPs was treated with 20 μL ProteoMiner™ beads to enrich HCPs. When the sample was treated with ProteoMiner™ beads and subsequently eluted with ProteoMiner™ elution buffer in combination with a cleaning step, such as acetone precipitation or FASP, 11 or 8 endogenous HCPs were identified as shown in Table 1. In contrast, using 8M Urea in 5% acetic acid as elution buffer without using a cleaning step was more effective for enrichment of HCPs from the sample, and the number of endogenous HCPs identified with high confidence was increased to 26 as shown in Table 1. The results suggested that the addition of a cleaning step, for example, a CHAPS removal step using acetone precipitation or FASP, can have negative impacts on HCP enrichments, since some HCPs were removed by the cleaning step.

TABLE 1

Enrichments of HCPs using ProteoMiner ™ beads

| ProteoMiner ™ Bead Amount | mAb1 Loading Amount | Elution Buffer | Cleaning Before Digestion | High Confidence Protein Number (>2 peptides) |
|---|---|---|---|---|
| 1 kit (10 mg capacity) | 10 mg | 8M urea in 5% acetic acid | N/A | 26 |

TABLE 1-continued

Enrichments of HCPs using ProteoMiner™ beads

| ProteoMiner™ Bead Amount | mAb1 Loading Amount | Elution Buffer | Cleaning Before Digestion | High Confidence Protein Number (>2 peptides) |
|---|---|---|---|---|
| 1 kit (10 mg capacity) | 10 mg | 8M urea, 2% CHAPS | Acetone precipitation | 11 |
| 1 kit (10 mg capacity) | 10 mg | 8M urea, 2% CHAPS | FASP | 8 |

In order to evaluate the effectiveness of different MS-compatible elution buffers, 13 purified HCPs from CHO (Chinese hamster ovary) cells at varying concentrations ranging from 0.1 ppm (0.1 ng HCP/mg mAb) to 200 ppm were spiked into 8 mg of purified monoclonal antibody, for example, mAb2. The purified mAb2 contained very low level of endogenous HCPs. The elution buffer of PTS or 6M guanidine showed stronger elution efficiency resulting in higher peptide amounts (26.1 or 22.8 μg, respectively) in comparison to the elution buffer of 8M urea in 5% acetic acid or 0.1% TFA/50% ACN (11.35 or 14.25 μg, respectively), as shown in Table 2. PTS buffer resulted in 60 proteins with high confidence including all 13 spiked-in HCPs. 8M urea resulted in 32 proteins with high confidence including 12 spiked-in HCPs. 6M guanidine resulted in 30 proteins with high confidence including 12 spiked-in HCPs. 0.1% TFA/50% CAN resulted 34 proteins with high confidence including 12 spiked-in HCPs. PTS buffer had the best HCP elution efficiency. Therefore, the combination of ProteoMiner™ beads and PTS elution buffer can significantly enrich HCPs in drug substance.

TABLE 2

HCP enrichments using 8 mg purified mAb2 with spiked-in HCPs (0.1-200 ppm)

| Sample amount (mAb2 + 0.1-200 ppm HCPs spiked-in) | Elution Buffer | Peptide Amount (μg) | Total ID | Number of Identified Spiked-in HCPs | High Confidence (>2 peptide) | DS PSM (heavy/light) |
|---|---|---|---|---|---|---|
| 8 mg | PTS | 26.1 | 106 | 13 | 60 | 11464/4806 |
| 8 mg | 8M urea in 5% AA | 11.35 | 65 | 12 | 32 | 8667/3888 |
| 8 mg | 6M guanidine | 22.8 | 64 | 12 | 30 | 12273/5283 |
| 8 mg | 0.1% TFA/50% ACN | 14.25 | 65 | 12 | 34 | 6860/2971 |

Example 2. Enrichment of HCPs Under Different pH Environments

Previous studies have shown that pH environments would affect ProteoMiner™ binding efficiency in different plant samples. Since ProteoMiner™ beads have not been used in HCP analysis previously, the binding efficiencies of therapeutic drug products to ProteoMiner™ beads in different pH environments were tested. The testing results indicated that drug substance showed preferable binding to ProteoMiner™ beads in basic condition as shown in Table 3. The PSM (peptide spectrum matches) number of drug substance in basic condition was 20% higher than that of acidic condition. PSM value indicates peptide spectra matched for the protein. About 35 endogenous HCPs were identified in basic condition (pH 9 Tris). About 66 endogenous HCPs were identified in acidic condition (pH 4 sodium acetate).

TABLE 3

HCP enrichments in different pH environments

| pH Environment | Peptide Amount | Total ID | High Confidence | DS PSM |
|---|---|---|---|---|
| Water (pH 6) | 20.92 | 142 | 58 | 11079/4645 |
| Sodium Acetate (pH 4) | 16.64 | 154 | 66 | 10795/5018 |
| Tris (pH 7.5) | 29.44 | 102 | 36 | 12537/5297 |
| Tris (pH 9) | 36.72 | 101 | 35 | 12910/5431 |

Example 3. Optimizing the Ratios of Sample to ProteoMiner™ Beads

The ratios of sample to ProteoMiner™ beads were optimized for conducting HCP enrichments. Each ProteoMiner™ kit contained 20 μL beads. 20 μL (1 kit) or 4 μL (⅕ kit) ProteoMiner™ beads were tested for the HCP enrichments. The ratios of sample to beads at 10 mg mAb1 to 20 μL ProteoMiner™ beads and at 2 mg mAb1 to 4 μL ProteoMiner™ beads were tested according to the manufacturer's suggestion. The results indicated that the amount of ProteoMiner™ beads did not affect the enrichment efficiency as shown in Table 4. Thus, 4 μL of ProteoMiner™ beads was preferred for testing the HCP enrichments. The optimal sample loading amount was also tested to achieve the best sensitivity. As shown in Table 5, 2 mg of loading sample amount showed 0.5 ppm sensitivity using mAb2 spiked-in sample.

detection limit was as low as 0.05 ppm as shown in Tables 6 and 7. The results in triplicate are shown in Table 8. When the loading amount was increased by 4 fold from 2 mg to 8 mg, the detection limit increased to 0.1 ppm as shown in Table 9. The results indicated that the potential detection limit was 0.05 ppm using 15 mg sample loading. The results also indicated that increasing sample loading amount can effectively accumulate the low abundance proteins on ProteoMiner™ beads, thus improving the detection limit. The testing result also indicated that the detection limit of ProteoMiner™ beads under the optimal conditions can reach as low as 0.05 ppm.

TABLE 6

Evaluation of the optimal sample loading amount

| Sample Amount (mAb2 + 0.05-0.5 ppm HCPs spiked-in) | Elution Buffer | Detection Limit (ppm) | Peptide Amount | Total ID | Number of Identified Spiked-in HCPs | High Confidence Protein Number (>2 peptide) | DS PSM (heavy/light) |
|---|---|---|---|---|---|---|---|
| 4 mg | PTS | 0.1 | 24.95 | 47 | 10 | 21 | 11362/4640 |
| 8 mg | PTS | 0.1 | 22.5 | 65 | 11 | 27 | 11511/4776 |
| 15 mg | PTS | 0.05 | 19.15 | 62 | 12 | 27 | 11777/4913 |

TABLE 4

Optimization of the ratio of sample to ProteoMiner™ beads for conducting HCP enrichments

| Amount of ProteoMiner™ Beads | mAb1 Loading Amount | Elution Buffer | High Confidence Protein Number (>2 peptide) |
|---|---|---|---|
| 1/5 kit (4 μL, 2 mg capacity) | 2 mg | 8M urea in 5% AA | 25 |
| 1 kit (20 μL, 10 mg capacity) | 10 mg | 8M urea in 5% AA | 26 |

TABLE 7

Evaluation of the optimal detection limit

| Spiked in ppm | Protein Name | MW | Molar ppm | 4 mg (Unique Peptides) | 8 mg (Unique Peptides) | 15 mg (Unique Peptides) |
|---|---|---|---|---|---|---|
| 0.5 | Beta-hexosaminidase | 60.1k | 1.25 | 5 | 9 | 11 |
| 0.5 | hPLBD2 | 65k | 1.15 | 5 | 9 | 8 |
| 0.5 | Cathepsin Z | 34k | 2.21 | 7 | 10 | 10 |

TABLE 5

Optimization of sample loading amounts

| Sample Amount (mAb2 + 0.1-200 ppm HCPs spiked-in) | Elution Buffer | Detection Limit (ppm) | Number of Identified Spiked-in HCPs | High Confidence Protein Number (>2 peptide) | DS PSM | Match to IP Result (>2 peptide) |
|---|---|---|---|---|---|---|
| 2 mg | PTS | 0.5 | 12 | 38 | 10582/4306 | 12 |
| 8 mg | PTS | 0.1 | 13 | 58 | 9285/3842 | 16 |

In order to evaluate the optimal sample loading amount and detection limit, 11 purified HCPs from CHO cells with varied concentrations ranging from 0.05 ppm to 0.5 ppm were spiked into different amount of purified mAb2 for testing. To test the bias of enrichment preference of ProteoMiner™ beads, the spiked-in proteins not only varied in concentration, but also varied in size. All of 0.5 ppm spiked-in HCPs can be found with only 4 mg sample loading. Most of the 0.1 ppm spiked-in HCPs can be found in 8 mg sample loading. Although most of the spiked-in proteins with concentration above 0.1 ppm can be identified in 4 mg sample loading, 8 mg sample loading showed better coverage in most of proteins which had low concentrations. When loading sample was further increased to 15 mg, the TABLE 7-continued Evaluation of the optimal detection limit

| Spiked in ppm | Protein Name | MW | Molar ppm | 4 mg (Unique Peptides) | 8 mg (Unique Peptides) | 15 mg (Unique Peptides) |
|---|---|---|---|---|---|---|
| 0.5 | Metalloproteinase inhibitor 1 | 22.4k | 3.35 | 5 | 6 | 7 |
| 0.5 | Transtheyretin | 17k | 4.41 | 5 | 5 | 6 |
| 0.1 | Carboxypeptidase | 54.2k | 0.28 | n/a | 2 | 4 |
| 0.1 | Cathepsin D | 44.1k | 0.34 | 3 | 6 | 7 |
| 0.1 | peptidyl-prolyl cis-trans isomerase | 23.6 | 0.64 | 4 | 8 | 11 |
| 0.1 | c-x-c motif chemokine | 11k | 1.36 | 3 | 2 | 3 |

TABLE 7-continued

Evaluation of the optimal detection limit

| Spiked in ppm | Protein Name | MW | Molar ppm | 4 mg (Unique Peptides) | 8 mg (Unique Peptides) | 15 mg (Unique Peptides) |
|---|---|---|---|---|---|---|
| 0.05 | LAL (half dimer/monomer) | 45.6k | 0.11 | n/a | n/a | 1 |
| 0.05 | Acid ceramidase | 44.7k | 0.17 | 2 | 4 | 12 |

TABLE 8

Replicates of 15 mg loading.

| Spiked in ppm | Protein name | MW | Molar ppm | 15 mg (Replicate 1) | 15 mg (Replicate 2) | 15 mg (Replicate 3) |
|---|---|---|---|---|---|---|
| 0.5 | Beta-hexosaminidase | 60.1k | 1.25 | 8 | 10 | 9 |
| 0.5 | hPLBD2 | 65k | 1.15 | 9 | 9 | 9 |
| 0.5 | Cathepsin Z | 34k | 2.21 | 11 | 12 | 12 |
| 0.5 | Metalloproteinase inhibitor 1 | 22.4k | 3.35 | 6 | 5 | 7 |
| 0.5 | Transtheyretin | 17k | 4.41 | 8 | 8 | 8 |
| 0.1 | Cathepsin D | 44.1k | 0.34 | 6 | 11 | 8 |
| 0.1 | peptidyl-prolyl cis-trans isomerase | 23.6 | 0.64 | 8 | 8 | 9 |
| 0.1 | c-x-c motif chemokine | 11k | 1.36 | 2 | 3 | 3 |
| 0.05 | LAL (half dimer/monomer) | 45.6k | 0.11 | 1 | 1 | 2 |
| 0.05 | Acid ceramidase | 44.7k | 0.17 | 5 | 10 | 7 |

TABLE 9

Increasing sample loading amount by 4 folds

| Spiked-in | Protein Name | 2 mg (unique peptides) | 8 mg (unique peptides) |
|---|---|---|---|
| 200 | Beta-hexosaminidase | 21 | 22 |
| 100 | Carboxypeptidase | 28 | 30 |
| 50 | hPLBD2 | 10 | 11 |
| 20 | Cathepsin Z | 14 | 16 |
| 10 | SIAE | 13 | 15 |
| 10 | Cathepsin D | 15 | 16 |
| 5 | Metalloproteinase inhibitor 1 | 7 | 8 |
| 5 | peptidyl-prolyl cis-trans isomerase | 10 | 12 |
| 5 | LAL (half dimer/monomer) | 9 | 10 |
| 1 | c-x-c motif chemokine | 3 | 3 |
| 1 | Transtheyretin | 5 | 6 |
| 0.5 | Acid ceramidase | 10 | 12 |
| 0.1 | Procollagen C endopeptidase enhancer 1 | x | 2 |

Figure 2A:
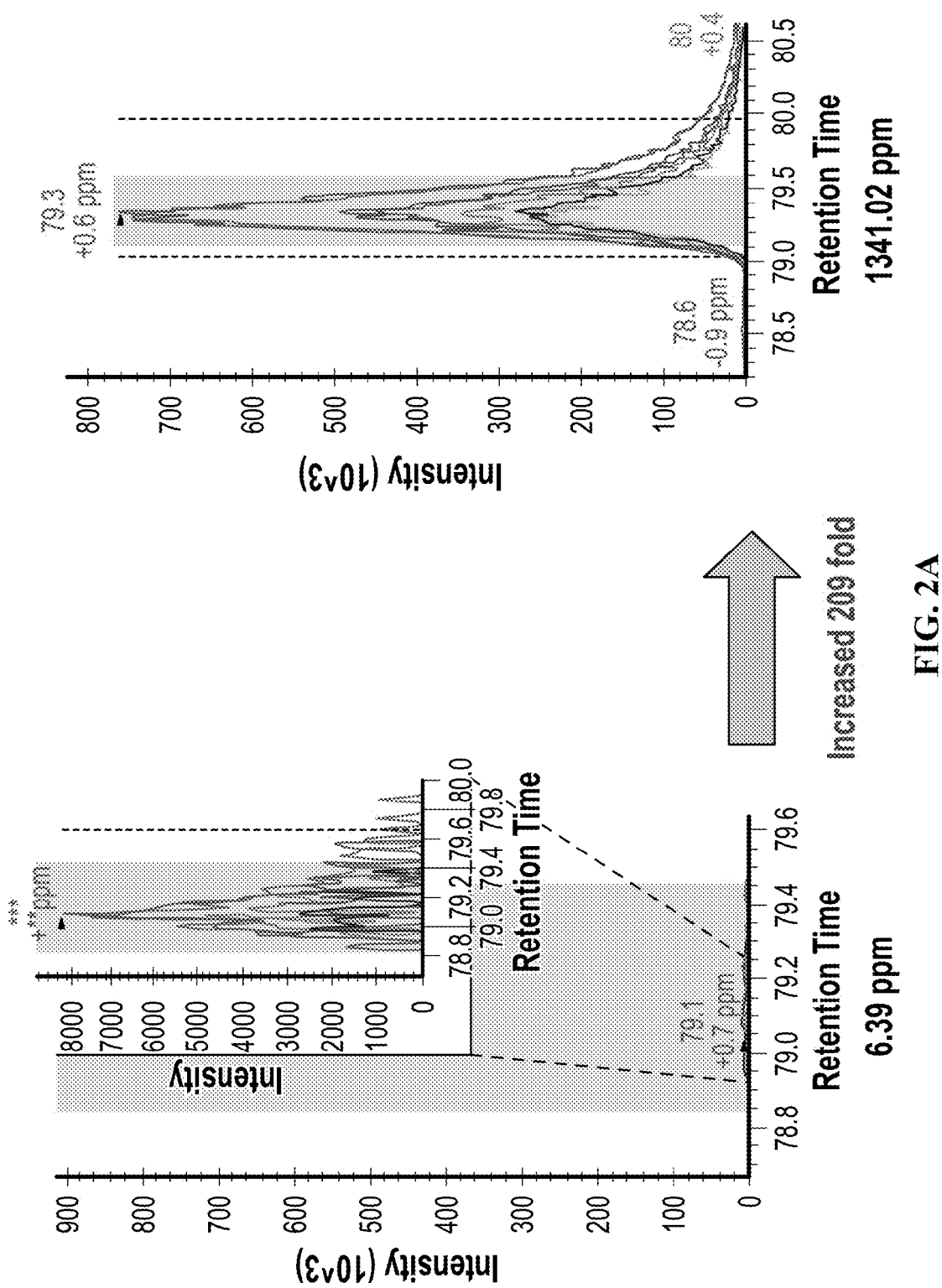
FIG. 2A shows PRM signal changes of one HCP peptide, for example, IYVASVHQDLSDDDIK (SEQ ID NO: 1), derived from Poly-binding-splicing Factor PUF60 according to an exemplary embodiment.
Figure 2B:
FIG. 2B shows PRM signal changes of one HCP peptide, for example, TYFLKPSK (SEQ ID NO: 2), derived from Protein NipSnap homolog 3B according to an exemplary embodiment.
Figure 2B:
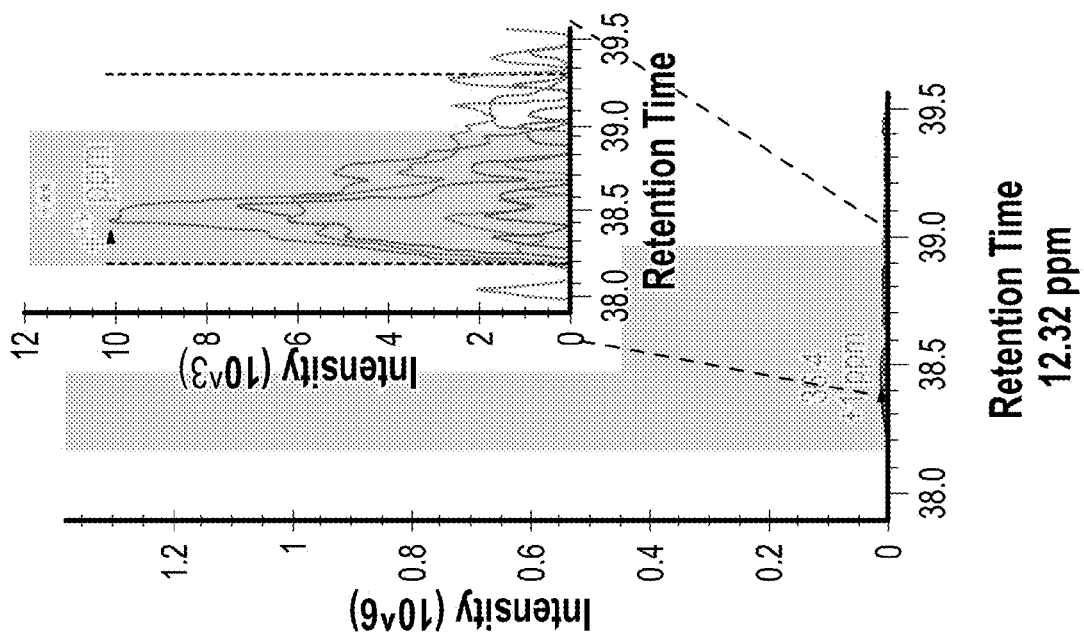

To evaluate the dynamic range reduction, PRM analysis, for example, a targeting MS approach, was performed to calculate the HCP enrichment factor resulting from the ProteoMiner™ method. By comparing the relative abundance of individual HCP peptides versus antibody peptides before and after contacting ProteoMiner™ beads, the HCP enrichment factor can be calculated. FIG. 2A showed PRM signal changes of one HCP peptide, for example, IYVASVHQDLSDDDIK (SEQ ID NO: 1), derived from one of the known HCPs, for example, Poly-binding-splicing Factor PUF60. FIG. 2B shows PRM signal changes of another HCP peptide, for example, TYFLKPSK (SEQ ID NO: 2) derived from Protein NipSnap homolog 3B which was a newly discovered HCP in this study. Both example peptides demonstrated more than 200-fold increases in the PRM signal after ProteoMiner™ bead treatment. By enriching low abundance HCPs, the protein dynamic range in ProteoMiner™ treated samples was significantly reduced, which resulted the increased signal to noise ratio in the subsequent MS analysis.

Example 4. Evaluation of Method Reproducibility

NISTmAB standard was used to evaluate the reproducibility of the HCP enrichment method of the present application using ProteoMiner™ beads and PTS buffer. The workflow of the HCP enrichment method of the present application included the step of washing ProteoMiner™ beads in spin column with 200 µL PBS followed by centrifugation at 1000 rcf for 30 seconds to remove buffer and repeating the same step twice. The step of resuspending beads with 200 µL PBS was followed by transferring 40 µL bead suspension solution to a tube. 15 mg of sample at 50 mg/mL was added into the tube to be mixed with the bead suspension under rotation for 2 hours at room temperature. The mixture of beads and sample was loaded into a tip with frit followed by centrifugation at 1000 rcf for 30 seconds. Subsequently, the supernatant was removed from the tube. Thereafter, the beads were washed with 100 µL PBS followed by centrifugation at 200 rcf for 1 minute to remove supernatant. The beads were washed again. Subsequently, 10 µL PTS buffer was used to elute proteins from beads. The beads were fully resuspended in PTS buffer followed by centrifugation at 200 rcf for 1 minute to collect the eluent in supernatant. The same step was repeated twice. The eluent was heated at 95° C. for 5 minutes. Subsequently, the eluent was diluted 5 times using buffer (100 mM Tris-HCl pH 8.0). 1 µg trypsin was added to the diluted eluent for overnight digestion to obtain a solution containing peptide mixture. Subsequently, 10% TFA was added to the peptide mixture solution at final concentration of 0.1% TFA. Subsequently, the peptide mixture solution was centrifuged at 14000 rcf for 5 minutes to obtain precipitates and supernatant. A desalting process was conducted on the supernatant.

Figure 3A:
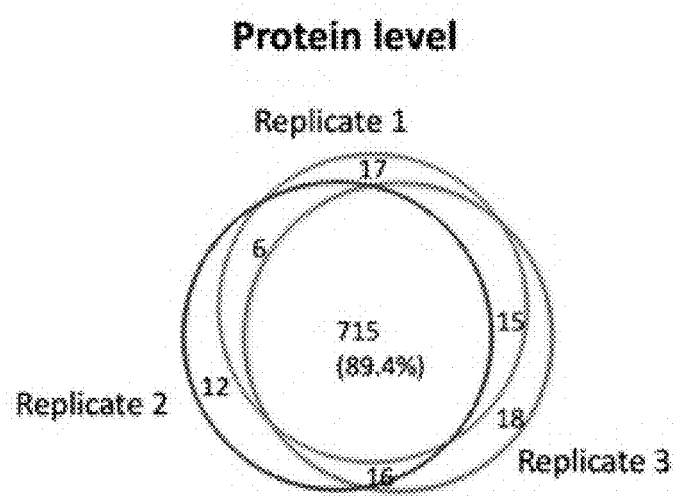
FIG. 3A shows the evaluation of the reproducibility of the HCP enrichment method of the present application using a triplicate experiment according to an exemplary embodiment.
Figure 3A:
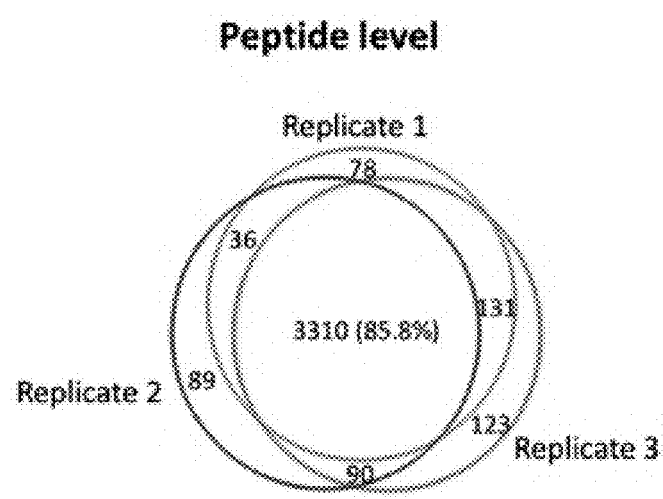
Figure 3B:
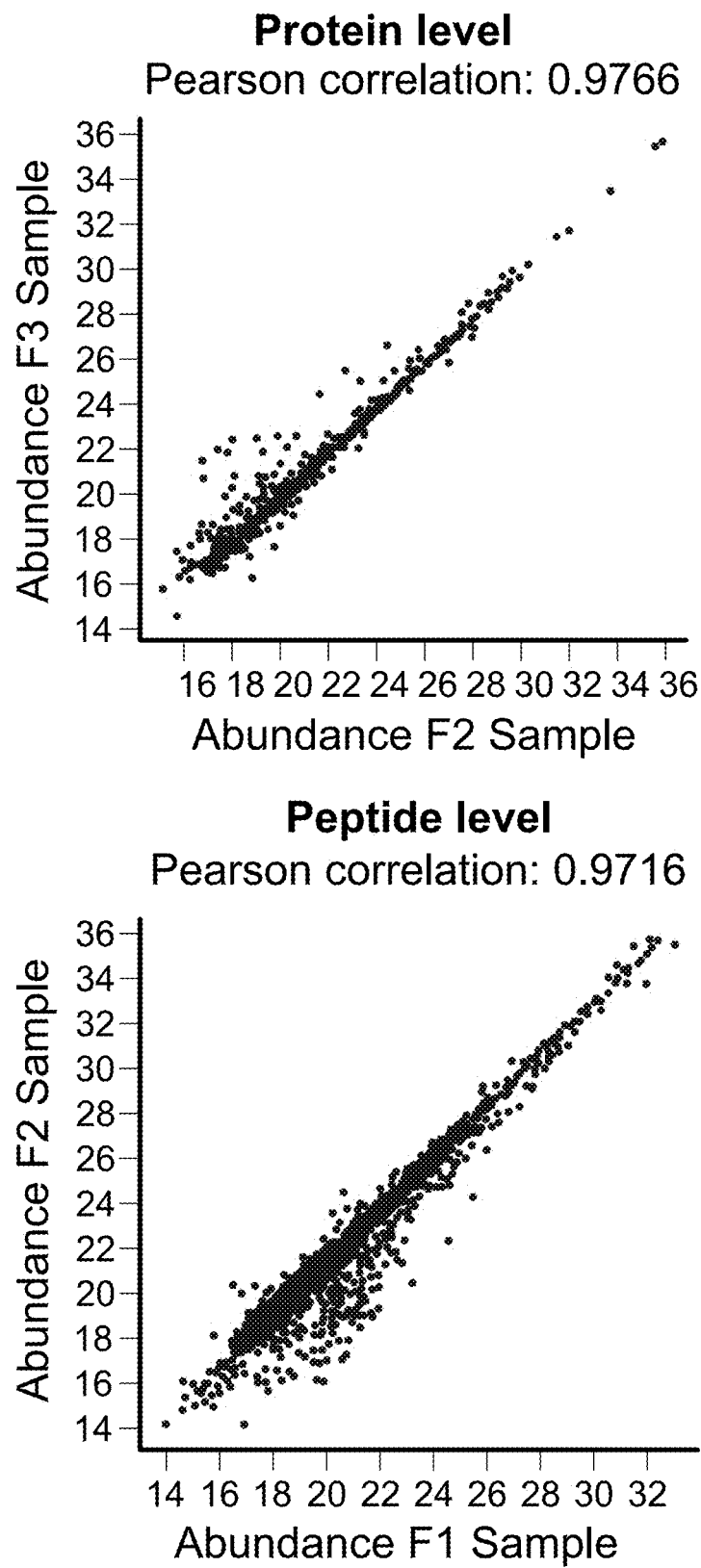
FIG. 3B shows the results of Pearson correlation analysis to evaluate the reproducibility of the HCP enrichment method of the present application according to an exemplary embodiment.

A triplicate experiment using NISTmAb standard was conducted to evaluate the reproducibility of the HCP enrichment method of the present application. As shown in FIG. 3A, in total across three runs, 715 common proteins equivalent to 89.4% of all proteins and 3310 common peptides equivalent to 85.8% of all peptides, were identified. The highly reproducible results indicated the high confidence in protein identification, which is crucial for the enrichment of HCPs. In addition, label-free quantitation was performed to quantify the relative amount of each peptide in all runs. As shown in FIG. 3B, the Pearson correlation analysis was greater than 0.97. It indicated that the HCP enrichment method of the present application using ProteoMiner™ beads and PTS buffer was highly reproducible with little variation.

Figure 4:
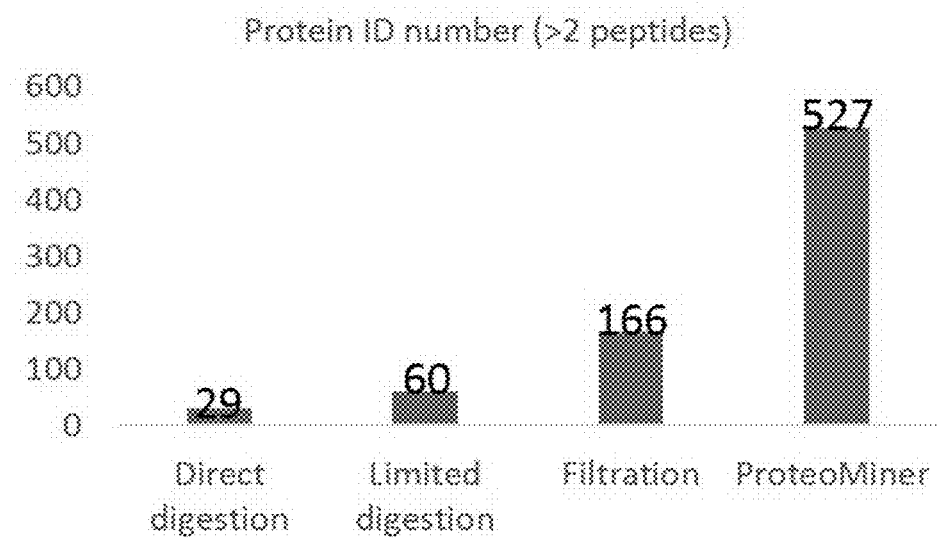
FIG. 4 shows the results of using the HCP enrichment method of the present application to identify HCPs using NISTmAb in comparing to the HCPs identified by Doneanu et al. and Huang et al. according to an exemplary embodiment.
Figure 4:
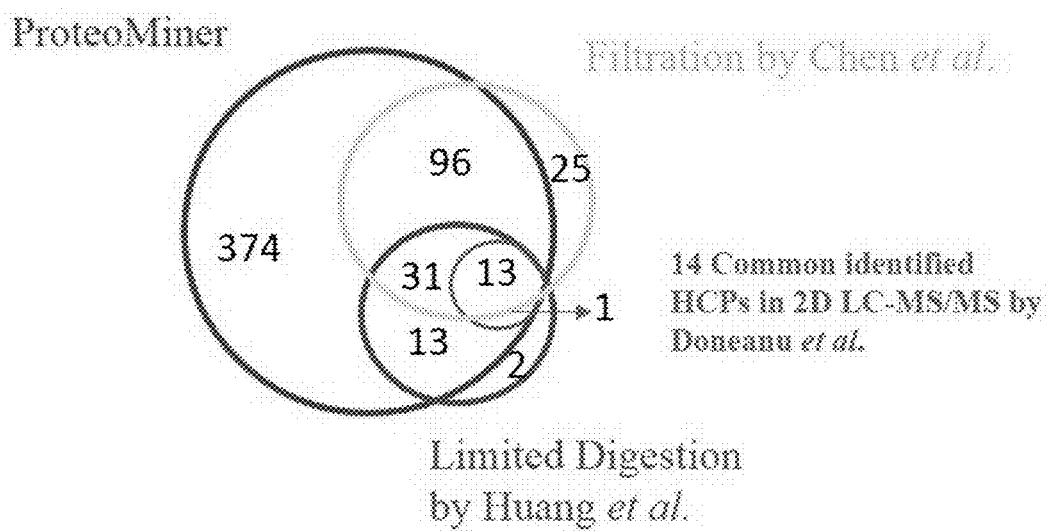

A total of 527 HCPs were identified with high confidence using the ProteoMiner™ method of the present application. Only 29 HCPs were identified using direct digestion. As shown in FIG. 4, in comparing the ProteoMiner™ and limited digestion methods, 58 HCPs were identified by both methods. In comparing the ProteoMiner™ and filtration methods, 140 HCPs were identified by both methods. These 140 HCPs were about 84% of the 166 HCPs which were identified by filtration method.

Example 5. Identification of HCPs Using NISTmAb Standard

The HCP enrichment method of the present application (using ProteoMiner™ beads and PTS buffer) was used to identify HCPs using NISTmAb standard, for example, RM 8670. A total of 527 HCPs, for example, mouse proteins, were identified with high confidence (more than 2 peptides identified) at a false positive rate of ≤0.01, while only 29 mouse proteins were identified using direct digestion as shown in FIG. 4. These 527 mouse proteins were compared to two previous studies, for example, Doneanu et al. and Huang et al., 14 HCPs and 59 HCPs with high confidence were identified by Doneanu et al. and Huang et al., respectively, using NISTmAb standard (RM 8670). As shown in FIG. 4, all of the 14 HCPs detected by Doneanu et al. and 58 of the 60 HCPs detected by Huang et al. were identified using the HCP enrichment method of the present application.

Ataxin-2 which was not detected by Doneanu et al. and Huang et al. was actually detected by the method of the present application, but only one peptide was identified. Phosphoglycerate kinase 2 was identified with two peptides in Huang et al. Phosphoglycerate kinase 1 which has 84% sequence similarity to phosphoglycerate kinase 2 was identified by the method of the present application with 17 unique peptides. In summary, 467 of the 527 identified mouse HCPs in the NISTmAb standard were not reported by Doneanu et al. and Huang et al. previously. Among these 467 mouse HCPs, 192 of these 467 mouse HCPs contain more than 5 unique peptides, and 330 of these 467 mouse HCPs contain greater or equal to 3 unique peptides.

Example 6. Validation of Identified HCPs by Parallel Reaction Monitoring

Parallel reaction monitoring (PRM) analysis was used to verify the identities of the HCPs which were identified using the HCP enrichment method of the present application (using ProteoMiner™ beads and PTS buffer). 25 of 527 identified NISTmAb HCPs were randomly selected for PRM analysis. The presence of the selected 25 HCPs in both direct digestion and ProteoMiner treated samples were confirmed by comparing peptide signals of these HCPs before and after ProteoMiner™ treatment. Improved efficiency of the ProteoMiner method was also validated by PRM validation. The selected HCPs were found to be enriched about 13-1109 fold using the ProteoMiner™ method as shown in Tables 10 and 11. Table 10 listed the HCPs that were identified by Doneanu et al. and Huang et al. 82% of the selected HCPs were measured to be present at higher than 1 ppm in direct digestion sample, which was consistent with the results from Huang et al. Table 11 lists the novel HCP targets that were detected and identified by the HCP enrichment method of the present application.

TABLE 10

HCPs identified by Doneanu et al. and Huang et al.

| Accession No. | Protein Name | Direct Digestion (ppm) | ProteoMiner™ Treated (ppm) | Improved Enrichment (fold) |
| --- | --- | --- | --- | --- |
| P06745 | Glucose-6-phosphate isomerase | 56.66 | 2724.75 | 48.09 |
| P08249 | Malate dehydrogenase, mitochondrial | 1.97 | 2181.28 | 1109.53 |
| P09041 | Phosphoglycerate kinase 2 | 2.58 | 306.18 | 118.51 |
| P40124 | Adenylyl cyclase-associated protein 1 | 0.83 | 91.80 | 111.06 |
| P40142 | Transketolase | 8.01 | 1631.28 | 203.62 |
| P53996 | Cellular nucleic acid-binding protein | 3.28 | 132.11 | 40.28 |
| Q3UEB3 | Poly(U)-binding-splicing factor PUF60 | 6.39 | 1341.02 | 209.76 |
| Q60864 | Stress-induced-phosphoprotein 1 | 38.91 | 4870.95 | 125.20 |
| Q6PGH2 | Jupiter microtubule associated homolog 2 | 0.39 | 31.73 | 81.77 |
| Q8BGD9 | Eukaryotic translation initiation factor 4B | 1.31 | 17.90 | 13.63 |
| Q8BND5 | Sulfhydryl oxidase 1 | 4.45 | 205.21 | 46.14 |
| Q8CGC7 | Bifunctional glutamate/proline-RNA ligase | 0.20 | 63.28 | 316.02 |
| Q91YR9 | Prostaglandin reductase 1 | 12.13 | 758.13 | 62.50 |
| Q923D2 | Flavin reductase (NADPH) | 19.40 | 2372.69 | 122.28 |
| Q99KN9 | Clathrin interactor 1 | 77.54 | 2150.39 | 27.73 |
| Q9CZ44 | NSFL1 cofactor p47 | 30.46 | 1704.85 | 55.96 |
| Q9DBP5 | UMP-CMP kinase | 25.36 | 4039.94 | 159.30 |

TABLE 11

Selected novel targets identified by the HCP enrichment method of the present application

| Accession No. | Protein Name | Direct Digestion (ppm) | ProteoMiner ™ Treated (ppm) | Improved Enrichment (fold) |
|---|---|---|---|---|
| F6ZDS4 | Nucleoprotein TPR | 1.81 | 283.73 | 156.69 |
| P48678 | Prelamin-A/C | 0.18 | 76.47 | 414.37 |
| P50580 | Proliferation-associated protein | 2.13 | 219.16 | 102.78 |
| P56213 | FAD-linked sulfhydryl oxidase | 0.28 | 87.90 | 313.89 |
| P62075 | Mitochondrial import inner membrane translocase subunit Tim13 | 4.33 | 922.67 | 213.10 |
| P97855 | Ras GTPase-activating protein-binding protein 1 | 1.82 | 715.24 | 392.03 |
| Q9CQE1 | Protein NipSnap homolog 3B | 12.32 | 3093.73 | 251.12 |
| Q9JIY5 | Serine protease HTRA2, mitochondrial | 3.68 | 366.36 | 99.60 |

The results showed substantially improved sensitivity using the ProteoMiner™ method of the present application. Although most of the proteins measured were present at very low level before ProteoMiner™ treatment, the relative concentrations of the same proteins were substantially increased after the ProteoMiner™ treatment. The sensitivities in detecting these low abundance proteins were improved significantly, since most HCPs were enriched more than 100 fold as shown in Tables 10 and 11. In particular, one selected HCP was enriched more than 1000 fold as shown in Table 10. The ProteoMiner™ method of the present application was able to increase the signal of each HCP significantly to reduce the dynamic range of the protein concentrations in the sample.

Example 7. Comparison Between Filtration Method and ProteoMiner™ Method

Figure 5A:
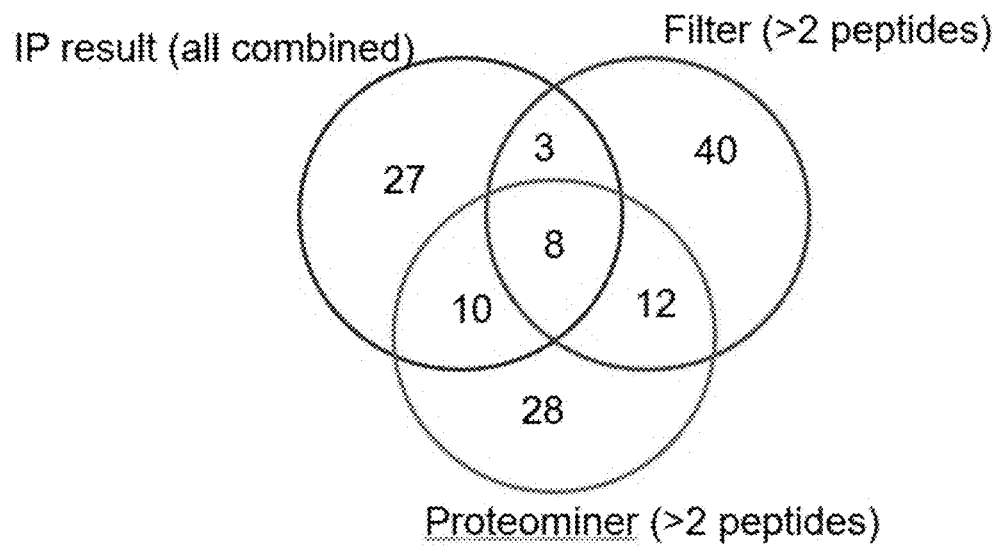
FIG. 5A shows the results of detecting and identifying HCPs in samples containing mAb3 and 13 spiked-in HCPs by comparing the filtration (filter) and ProteoMiner™ methods according to an exemplary embodiment.
Figure 5B:
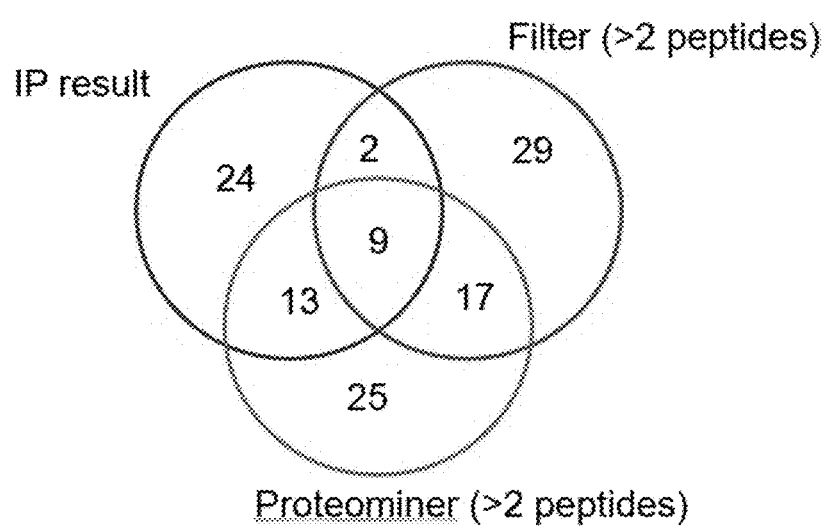
FIG. 5B shows the results of detecting and identifying HCPs in samples containing mAb4 and HCP impurities by comparing the filtration (filter) and ProteoMiner™ methods according to an exemplary embodiment.

The efficiencies of HCP enrichments were compared between ProteoMiner™ and filtration (filter) method for the detection and identification of HCPs in samples containing antibodies. 1.5 mg of mAb3 and HCPs were dissociated in SDC and SLS cocktail buffer, after dissociation, the HCPs can be separated from antibody by applying 50K MWCO filter. (Chen et al. Improved Host Cell Protein Analysis in Monoclonal Antibody Products through Molecular Weight Cutoff Enrichment. *Analytical Chemistry* 2020 92 (5), 3751-3757). The numbers of HCPs which were identified with two peptides are shown in FIG. 5A and FIG. 5B for filter and ProteoMiner™ methods (The IP result is the combined result that from all different lots of mAb3 and mAb4.). The testing results of the spiked-in HCPs were shown in Table 12. Thirteen purified HCPs from CHO cells with varied concentrations ranging from 0.1 ppm to 200 ppm were spiked into samples containing purified mAb3 for testing. As shown in Table 12, ProteoMiner™ method showed higher identified PSM and higher unique peptides overall.

TABLE 12

Comparison between Filter method and ProteoMiner ™ method for spiked-in HCPs

| Spiked-in Final ppm | Protein Name | Molecular Weight | Identified psm (filter) | Unique Peptides (filter) | Identified psm (ProteoMiner ™) | Unique Peptides (ProteoMiner ™) |
|---|---|---|---|---|---|---|
| 200 | Beta-hexosaminidase | 60.1k | 64 | 10 | 116 | 22 |
| 100 | Carboxypeptidase | 54.2k | 240 | 25 | 268 | 30 |
| 50 | hPLBD2 | 65k | 8 | 3 | 362 | 11 |
| 20 | Cathepsin Z | 34k | 62 | 17 | 327 | 16 |
| 10 | SIAE | 61.4k | n/a | n/a | 81 | 15 |
| 10 | Cathepsin D | 44.1k | 12 | 4 | 211 | 16 |
| 5 | Metalloproteinase inhibitor 1 | 22.4k | 13 | 3 | 46 | 8 |
| 5 | LAL (half dimer/monomer) | 45.6k | n/a | n/a | 99 | 10 |
| 5 | peptidyl-prolyl cis-trans isomerase | 23.6k | 96 | 11 | 108 | 12 |
| 1 | c-x-c motif chemokine | 11k | 31 | 4 | 26 | 3 |

TABLE 12-continued

Comparison between Filter method and ProteoMiner™ method for spiked-in HCPs

| Spiked-in Final ppm | Protein Name | Molecular Weight | Identified psm (filter) | Unique Peptides (filter) | Identified psm (ProteoMiner™) | Unique Peptides (ProteoMiner™) |
|---|---|---|---|---|---|---|
| 1 | Transtheyretin | 17k | 34 | 4 | 36 | 6 |
| 0.5 | Acid ceramidase | 44.7k | n/a | n/a | 52 | 12 |
| 0.1 | Procollagen C endopeptidase enhancer 1 | 55.2k | n/a | n/a | 4 | 2 |

Example 8. Repeatability Test

Figure 6:
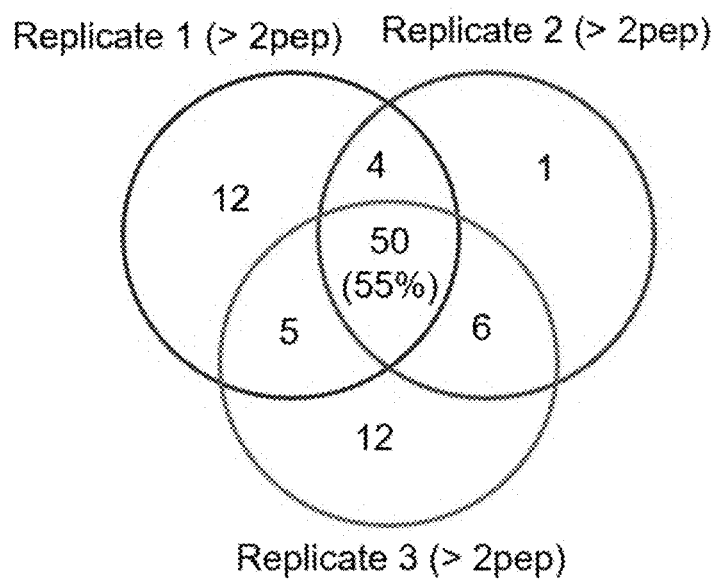
FIG. 6 shows the results of testing repeatability of the ProteoMiner™ method of the present application for HCP enrichment using samples containing mAb4 and HCP impurities according to an exemplary embodiment.
Figure 6:
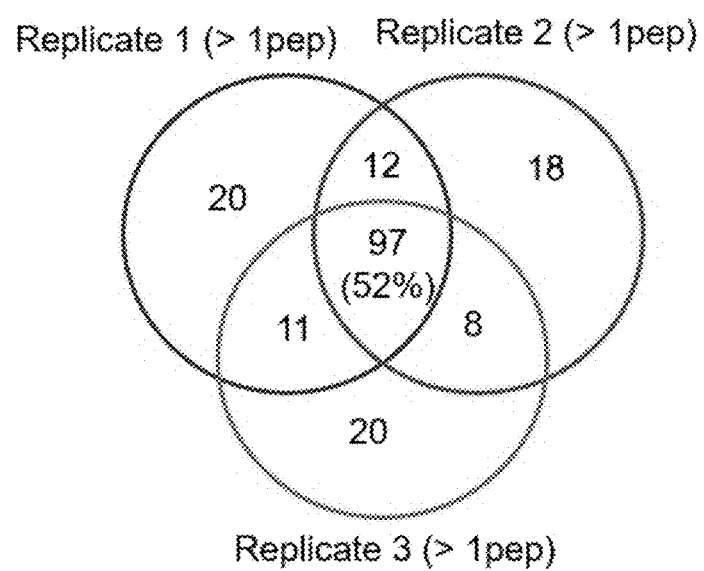

The repeatability of the ProteoMiner™ method of the present application for HCP enrichment was tested using mAb4. 15 mg of samples containing mAb4 and HCP impurities were tested using ⅕ of the ProteoMiner™ kit. Three replicates were conducted. As shown in Table 13 and FIG. 6, the results show good repeatability based on match to IP results.

TABLE 13

Repeatability tests of ProteoMiner™ method for HCP enrichment

| | Sample Amount | Peptide Amount | Total ID | High Confidence (>2 pep) | DS PSM (heavy/light) | Match to IP result (>2 pep) (total 48 targets from IP) | Match to IP result (include 1 pep) (total 48 targets from IP) |
|---|---|---|---|---|---|---|---|
| 1. | 15 mg | 21.7 | 142 | 73/(12) | 9733/4152 | 19 | 24 |
| 2. | 15 mg | 24.5 | 137 | 62/(10) | 10580/4579 | 19 | 25 |
| 3. | 15 mg | 22.35 | 138 | 74/(9) | 11264/4845 | 22 | 24 |

Example 9. Comparing ProteoMiner™ Method with Limited Digestion Method

Figure 7:
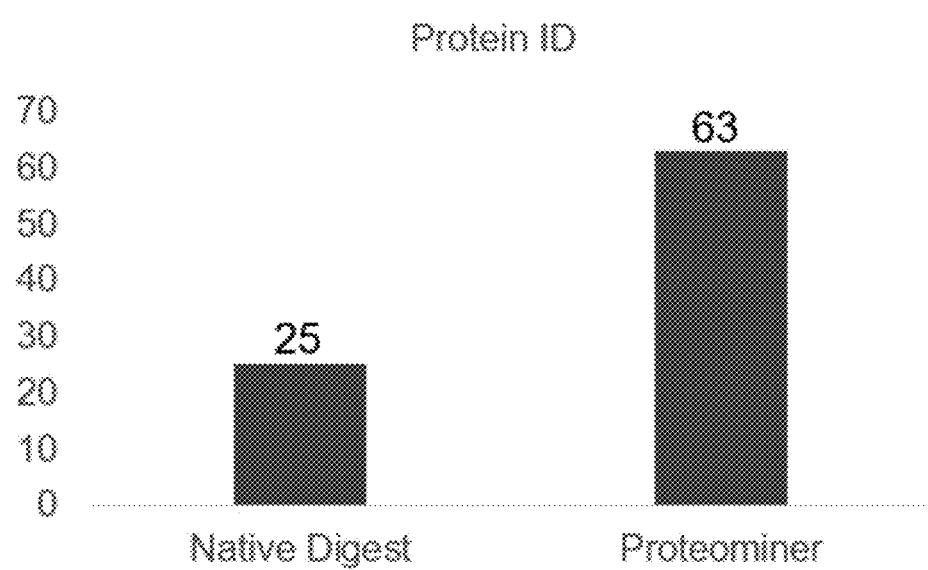
FIG. 7 shows efficiencies of native digestion and ProteoMiner™ methods for HCP enrichments using samples containing mAb5 and HCP impurities according to an exemplary embodiment.
Figure 8:
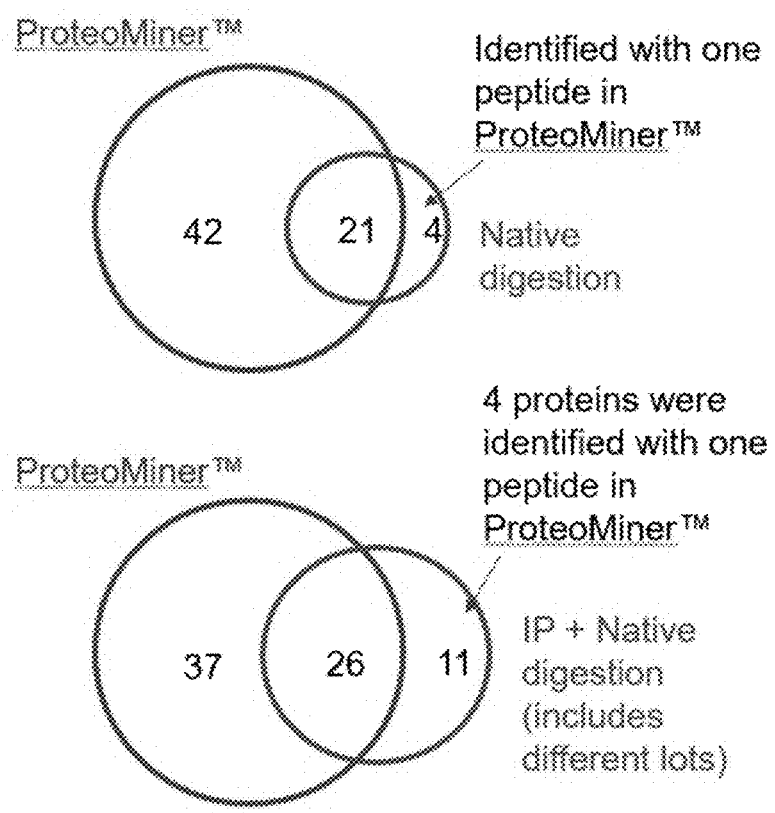
FIG. 8 shows the comparison of native digestion and ProteoMiner™ methods for the efficiencies of HCP enrichments according to an exemplary embodiments.

The efficiencies of native digestion and ProteoMiner™ methods for HCP enrichments were tested and compared using mAb5 containing HCP impurities. As shown in FIG. 7, a total of 63 HCPs were identified with high confidence using the ProteoMiner™ method of the present application. A total of 25 HCPs were identified with high confidence using the native digestion method. As shown in FIG. 8, in comparing the ProteoMiner™ and native digestion methods, 21 HCPs were identified by both methods. In comparing the ProteoMiner™ and native digestion methods, 26 HCPs were identified by both methods. Table 14 shows the 63 HCPs which were found in mAb5 sample using ProteoMiner™ method of the present application.

TABLE 14

HCPs found in mAb5 sample.

| Accession No. | Protein Name |
|---|---|
| G3I6T1 | Putative phospholipase B-like 2 |
| G3HXN7 | Beta-hexosaminidase |
| G3HLX3 | Alpha-N-acetylglucosaminidase |
| Q9JKY1 | Peroxiredoxin-1 |
| G3I4W7 | Cathepsin D |
| G3H892 | Aminoacylase-1A |
| G3I255 | L-lactate dehydrogenase |
| G3GZB2 | Acid ceramidase |
| G3H533 | Peptidyl-prolyl cis-trans isomerase |

TABLE 14-continued

HCPs found in mAb5 sample.

| Accession No. | Protein Name |
|---|---|
| G3IBF4 | Serine protease HTRA1 |
| G3I3N5 | V-type proton ATPase subunit C |
| G3I2K6 | Hippocalcin-like protein 1 |
| G3GR64 | Inter-alpha-trypsin inhibitor heavy chain H5 |
| G3GRS9 | N-acetylgalactosamine-6-sulfatase |
| G3IBH0 | Metalloproteinase inhibitor 1 |
| G3I3Y6 | Glutathione S-transferase P |
| G3I1V3 | Fibronectin |
| A0A061IFE2 | Liver carboxylesterase 1-like protein |
| G3GUR1 | Complement C1r-A subcomponent |
| G3GXZ0 | Protein-glutamine gamma-glutamyltransferase 2 |
| G3I8R9 | 78 kDa glucose-regulated protein |
| G3HGW6 | Laminin subunit alpha-5 |
| G3I7U9 | Serine protease HTRA2, mitochondrial |
| G3GVH3 | Uncharacterized protein C17orf39 |
| A0A061IQB8 | Ubiquitin-60S ribosomal protein L40-like isoform 2 |
| G3IAQ0 | Alpha-enolase |
| G3IFA9 | Transcription elongation factor B polypeptide 2 |
| G3II12 | Calcium-binding protein 39 |
| G3I3K5 | G-protein coupled receptor 56 |
| G3I5N6 | Insulin-like growth factor-binding protein 4 |
| G3HXL1 | Poly(RC)-binding protein 1 |
| G3HH30 | Aldose reductase |
| Q9EPP7 | Cathepsin Z |
| Q9WV24 | Beta-2-microglobulin |
| A0A061HWZ7 | Exosome complex component RRP46-like protein |
| A0A061II04 | Protein S100 |
| G3HI03 | U4/U6 small nuclear ribonucleoprotein Prp4 |
| A0A061IB69 | Fructose-bisphosphate aldolase |
| G3I5L3 | Annexin |

TABLE 14-continued

HCPs found in mAb5 sample.

| Accession No. | Protein Name |
|---|---|
| A0A061IDC7 | Sp110 nuclear body protein |
| G3H935 | Tyrosine-tRNA ligase |
| A0A061I0W7 | Brain-specific serine protease 4-like protein |
| G3IEU2 | Protein DJ-1 |
| P22629 | Streptavidin |
| A0A061IMN7 | Anionic trypsin-2-like protein |
| A0A061IK25 | Protein-L-isoaspartate |
| A0A061INB9 | C-X-C motif chemokine |
| A0A061I4J0 | Prefoldin subunit 2-like protein |
| G3IG05 | Annexin |
| A0A061I1Y4 | Perilipin-4-like protein |
| A0A061IEQ5 | Sphingomyelin phosphodiesterase |
| A0A061IKI0 | EF-HAND 2 containing protein |
| A0A061I523 | Procollagen C-endopeptidase enhancer 1 |
| G3HIM4 | Cell division control protein 42-like |
| G3H2A5 | Vacuolar protein sorting-associated protein 29 |
| G3GV64 | Mammalian ependymin-related protein 1 |
| G3HPZ5 | Macrophage-capping protein |
| G3HD94 | Desmoplakin |
| G3HAN8 | Adenosylhomocysteinase |
| A0A061I2S4 | Putative out at first protein like protein (Fragment) |
| A0A061HXN7 | Gelsolin |
| G3HN65 | Ras suppressor protein 1 |
| G3HH39 | Elongation factor 1-alpha 1 |
| G3IKC3 * | Glutathione S-transferase Mu 6 |
| G3GVW2 * | Putative hydrolase RBBP9 |
| G3GTT2 * | C-C motif chemokine |
| G3I4E8 * | Fatty acid-binding protein, adipocyte |

What is claimed is:

1. A method of identifying at least one host cell protein (HCP) impurity in a sample, comprising:
   contacting a sample to a solid support,
   wherein said sample includes at least one high-abundance peptide or protein and at least one HCP impurity,
   wherein interacting peptide ligands have been attached to said solid support, and
   wherein said at least one HCP impurity can bind to said interacting peptide ligands;
   washing said solid support using an elution solution to produce an eluate, wherein said elution solution includes at least one surfactant;
   subjecting said eluate to an enzymatic digestion condition to generate a peptide digest;
   subjecting said peptide digest to acidic conditions to produce an acidified peptide digest;
   centrifuging said acidified peptide digest to produce a surfactant-depleted peptide digest; and
   subjecting said surfactant-depleted peptide digest to mass spectrometry analysis to identify said at least one HCP impurity.

2. The method of claim 1, wherein the at least one surfactant is a phase transfer surfactant, an ionic surfactant, an anionic surfactant, a cationic surfactant, or combinations thereof.

3. The method of claim 1, wherein the at least one surfactant is sodium deoxycholate, sodium lauryl sulfate, sodium lauroyl sarcosinate, sodium dodecylbenzene sulphonate, or combinations thereof.

4. The method of claim 1, wherein a concentration of the at least one high-abundance peptide or protein is about at least 1000 times, 10,000 times, 100,000 times or 1,000,000 times higher than a concentration of the at least one HCP impurity.

5. The method of claim 1, wherein the interacting peptide ligands are a library of combinatorial hexapeptide ligands.

6. The method of claim 1, wherein the at least one HCP impurity is quantified using the mass spectrometer, wherein a detection limit of the at least one HCP impurity is about 0.05-0.1 ppm.

7. The method of claim 1, wherein the at least one high-abundance peptide or protein is an antibody, a bispecific antibody, an antibody fragment, a Fab region of an antibody, an antibody-drug conjugate, a fusion protein, a protein pharmaceutical product, or a drug.

8. The method of claim 1, wherein an enzyme of the enzymatic digestion condition is trypsin.

9. The method of claim 1, wherein the mass spectrometer is an electrospray ionization mass spectrometer, nano-electrospray ionization mass spectrometer, or a triple quadrupole mass spectrometer, wherein the mass spectrometer is coupled to a liquid chromatography system.

10. The method of claim 1, wherein the mass spectrometer is capable of performing LC-MS (liquid chromatography-mass spectrometry) or a LC-MRM-MS (liquid chromatography-multiple reaction monitoring-mass spectrometry) analyses.

11. A system for identifying at least one host cell protein (HCP) impurity in a sample, comprising:
a solid support;
interacting peptide ligands,
wherein said interacting peptide ligands are attached to said solid support, and
wherein said at least one HCP impurity can bind to the interacting peptide ligands;
an elution solution comprising at least one surfactant;
an enzymatic digestion solution;
an acidic solution;
a centrifuge; and
a mass spectrometer capable of identifying said at least one HCP impurity.

12. The system of claim 11, wherein the at least one surfactant is a phase transfer surfactant, an ionic surfactant, an anionic surfactant, a cationic surfactant, or combinations thereof.

13. The system of claim 11, wherein the at least one surfactant is sodium deoxycholate, sodium lauryl sulfate, sodium lauroyl sarcosinate, sodium dodecylbenzene sulphonate, or combinations thereof.

14. The system of claim 11, wherein a concentration of the at least one high-abundance peptide or protein is about at least 1000 times, 10,000 times, 100,000 times or 1,000,000 times higher than a concentration of the at least one HCP impurity.

15. The system of claim 11, wherein the interacting peptide ligands are a library of combinatorial hexapeptide ligands.

16. The system of claim 11, wherein a detection limit of the at least one HCP impurity is about 0.05-0.1 ppm.

17. The system of claim 11, wherein the at least one high-abundance peptide or protein is an antibody, a bispecific antibody, an antibody fragment, a Fab region of an antibody, an antibody-drug conjugate, a fusion protein, a protein pharmaceutical product, or a drug.

18. The system of claim 11, wherein an enzyme of the enzymatic digestion solution is trypsin.

19. The system of claim 11, wherein the mass spectrometer is an electrospray ionization mass spectrometer, nano-electrospray ionization mass spectrometer, or a triple quadrupole mass spectrometer, wherein the mass spectrometer is coupled to a liquid chromatography system.

20. The system of claim 11, wherein the mass spectrometer is capable of performing LC-MS (liquid chromatography-mass spectrometry) or a LC-MRM-MS (liquid chromatography-multiple reaction monitoring-mass spectrometry) analyses.

* * * * *